United States Patent [19]
Archer et al.

[11] Patent Number: 6,124,440
[45] Date of Patent: *Sep. 26, 2000

[54] CORES FOR TECHNETIUM RADIOPHARMACEUTICALS

[75] Inventors: Colin M. Archer, Buckinghamshire; Jonathan R. Dilworth; Panna Jobanputra, both of Essex; Ian A. Latham, Buckinghamshire; Russell M. Thompson, Essex, all of United Kingdom

[73] Assignee: Nycomed Amersham plc, United Kingdom

[*] Notice: This patent is subject to a terminal disclaimer.

[21] Appl. No.: 09/431,098

[22] Filed: Nov. 1, 1999

Related U.S. Application Data

[62] Division of application No. 08/774,299, Dec. 24, 1996, Pat. No. 6,001,979, which is a division of application No. 08/289,654, Aug. 12, 1994, Pat. No. 5,589,576, which is a continuation of application No. 07/689,763, filed as application No. PCT/GB90/01330, Aug. 28, 1990, abandoned.

Foreign Application Priority Data

Aug. 29, 1989 [GB] United Kingdom .................... 8919488

[51] Int. Cl.$^7$ ...................................................... C07F 13/00
[52] U.S. Cl. .............................. 534/14; 534/16; 424/1.53; 424/1.11
[58] Field of Search .................................. 424/1.11, 1.53, 424/1.65, 1.69, 1.73, 1.77, 9.1; 534/7, 10–16

[56] References Cited

U.S. PATENT DOCUMENTS

| | | |
|---|---|---|
| 4,387,087 | 6/1983 | Deutsch et al. . |
| 4,431,627 | 2/1984 | Eckelman et al. . |
| 4,481,184 | 11/1984 | Kronauge et al. . |
| 4,489,054 | 12/1984 | Deutsch et al. . |
| 4,781,912 | 11/1988 | Zanelli et al. . |
| 5,081,232 | 1/1992 | Latham et al. . |
| 5,116,596 | 5/1992 | Bremer et al. . |
| 5,164,175 | 11/1992 | Bremer et al. . |
| 5,206,370 | 4/1993 | Schwartz et al. . |
| 5,589,576 | 12/1996 | Archer et al. ............................. 534/14 |
| 6,001,979 | 12/1999 | Archer et al. ............................. 534/14 |

FOREIGN PATENT DOCUMENTS

| | | |
|---|---|---|
| 0 271 806 | 6/1988 | European Pat. Off. . |
| 0 291 281 | 11/1988 | European Pat. Off. . |
| 0 311 352 | 4/1989 | European Pat. Off. . |
| 0 384 769 | 8/1990 | European Pat. Off. . |
| 32 16026 | 11/1982 | Germany . |
| 2 101118 | 1/1983 | United Kingdom . |
| WO85/03063 | 7/1984 | WIPO . |

OTHER PUBLICATIONS

DuBois et al., *Nouveau J. De Chemie*, 1(16), 479–492 (1978).
Chisholm et al., *Comprehensive Coordination Chemistry*, 2, 161–189 (1987).
Bright et al., *Inorganic Chemistry*, 7(6), 1099–1117 (Jun. 1968).
Bright et al., *Inorganic Chemistry*, 8(4), 703–709 (Apr. 1969).
Goeden et al., *Inorganic Chemistry*, 22(1), 157–167 (1983).
Bradley et al., *J. Chem. Soc. Dalton Trans.*, 2651–2656 (1983).
Maatra et al., *Inorganic Chemistry*, 23, 2560–2561 (1984).
Chou et al., *J. Chem. Soc. Chem. Comm.*, 1184–1185 (1984).
Johnson et al., *Comprehensive Coordination Chemistry*, 101–159 (1988).
Nugent et al., *Coordination Chemistry Reviews*, 31, 123–175 (1980).
*Webster's Third New International Dictionary*, 1674, 1757, 1759, 1760 (1986).
M. Abercrombie et al., *A Dictionary of Biology*, 188–189 (1963).
A. Fritzberg et al., *Int. J. Nucl. Med. Biol.*, 9, 1–11 (1982).
Hsieh et al., *Inorganic Chemistry*, 26, 4079–4089 (1987).
Colton et al., *Aust. J. Chem.*, 17, 496–497 (1964).
McCleverty et al., *Transition Met. Chem.*, 12, 4–8 (1987).
Angelici et al., *Inorganic Chemistry*, 6(5), 988–998 (May 1967).
Chatt et al., *Inorganic Chemistry*, 21, 2383–2391 (1982).
Moore et al., *Inorganic Chemistry*, 6(5), 998–1003 (May 1967).
Nicholson et al., *Inorganic Chemistry*, 28(20), 3813–3819 (Oct. 1989).
*Academic Press Dictionary of Science and Technology*, C. Morris, Ed., 1292 (1992).
S. Olexa et al., *Biochemistry*, 20(21), 6139–6145 (1981).
*Funk & Wagnalls Standard College Dictionary*, 1047 (1974).

Primary Examiner—Jose' G. Dees
Assistant Examiner—Dameron Jones
Attorney, Agent, or Firm—Wenderoth, Lind & Ponack, L.L.P.

[57] ABSTRACT $^{99m}$Tc complexes of formula $L_n$Tc=NR, $L_n$Tc—N=NY, or $L_n$Tc—(N=NY)$_2$ wherein each L is independently a monodentate or multidentate ligand;
Y is a substituted or unsubstituted aryl group or substituted or unsubstituted alkyl group;
R is Y or the grouping —NR$^1$R$^2$;
n is 1–4;

where at least one of R or Y is combined with one or more of the L groups; R$^1$ and R$^2$ are H, substituted or unsubstituted aryl groups or substituted or unsubstituted aliphatic or cyclic alkyl groups, and are the same or different, provided that both are not hydrogen.

3 Claims, 1 Drawing Sheet

Fig 1  Pluto Plot of [Tc(Ntol)Cl$_3$(PPh$_3$)$_2$]
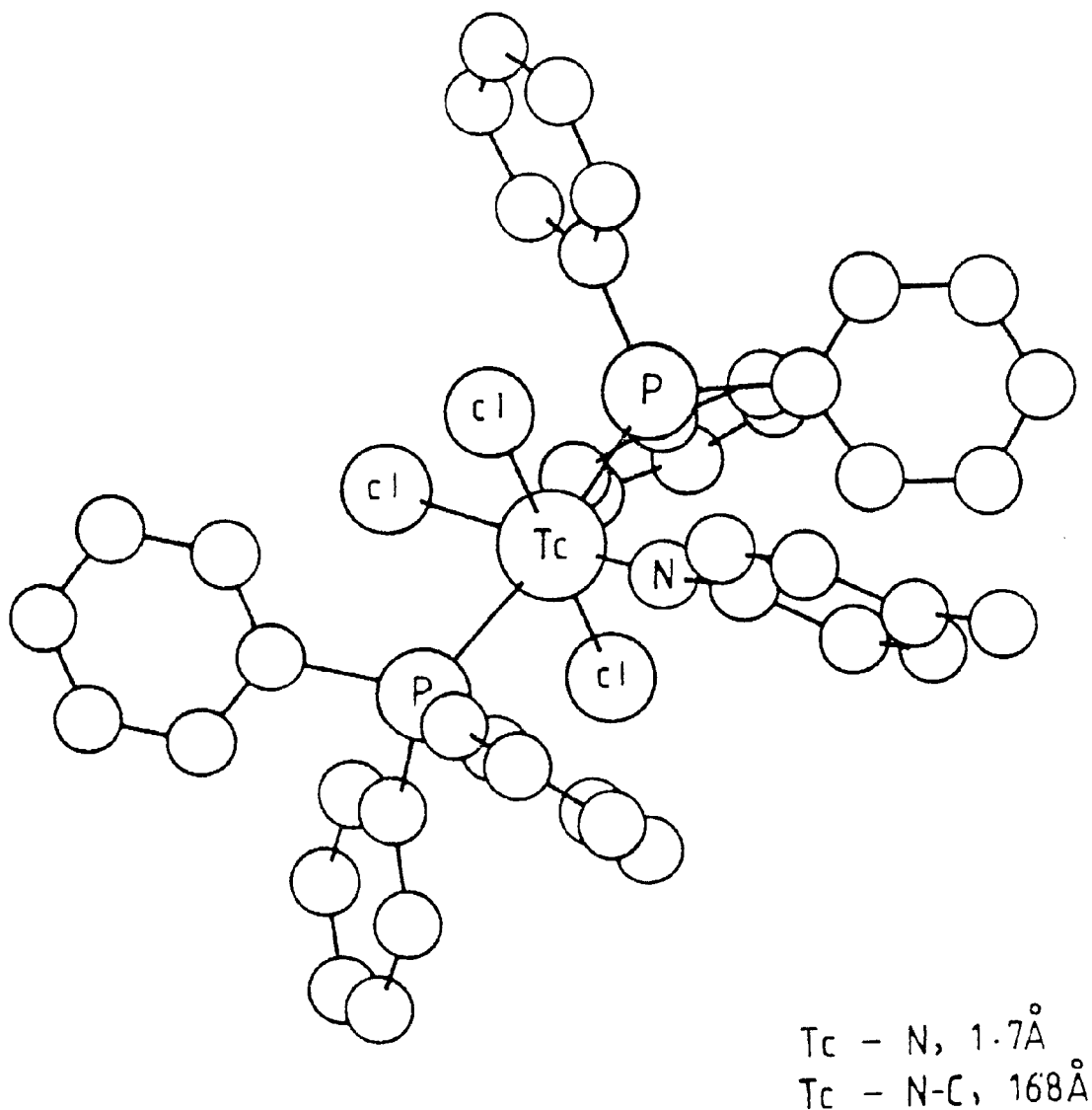
Tc — N, 1·7Å
Tc — N-C, 168Å

CORES FOR TECHNETIUM RADIOPHARMACEUTICALS

This is a divisional of Ser. No. 08/774,299, filed Dec. 24, 1996, now U.S. Pat. No. 6,001,979 which is a divisional of Ser. No. 08/289,654, filed Aug. 12, 1994, now U.S. Pat. No. 5,589,576, which is a continuation of Ser. No. 07/689,763, filed May 29, 1991, now abandoned, which is a 371 of PCT/GB90/01330, filed Aug. 28, 1990.

This invention relates to novel complexes of technetium (Tc), containing the moiety Tc≡NR, Tc—N≡NY or Tc(—N≡NY)$_2$, and their use in radiopharmaceuticals for a variety of clinical applications. Methods for the preparation of the technetium complexes are also described.

Radiopharmaceuticals may be used as diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which, because of physical or metabolic properties of its co-ordinated ligands, localises in a specific organ after intravenous injection. The resultant images can reflect organ structure or function. These images are obtained by means of a gamma camera that detects the distribution of ionising radiation emitted by the radioactive molecules. The principal isotope currently used in clinical diagnostic nuclear medicine is metastable technetium-99m ($^{99m}$Tc) and which has a half-life of 6 hours.

BRIEF DESCRIPTION OF THE DRAWING

FIG. 1 is a ball and stick representation of the complex molecule, [Tc(NC$_6$H$_4$CH$_3$)Cl$_3$(PPh$_3$)$_2$].

The preparation of $^{99m}$Tc radiopharmaceuticals generally requires addition of generator-produced Na$^{99m}$TcO$_4$ eluate to a ligand or ligands in the presence of a reducing agent. Many reducing agents have been used to this effect including tin metal, stannous ion, sodium borohydride, ferrous ascorbate, ferrous ion and formamidine sulphonic acid. These procedures often lead to Tc complexes containing the Tc=O moiety, where the technetium is in the +4 or +5 oxidation state. The formation of such radiopharmaceutical complexes can often occur via substitution reactions on [Tc$^V$OX$_5$]2– or [Tc$^{IV}$X$_6$]$^{2-}$ molecules, which has been identified as a route of significant synthetic utility (Deutsch E, Libson K, Jurisson S, Lindoy L F, Technetium Chemistry and Technetium Radiopharmaceuticals, Prog. Inorg. Chem. (1982) 30 p 175). Only under harsh reaction conditions in the presence of powerful reducing agents and/or strong acids or bases are Tc$^I$ oxidation state complexes attained and stabilised. A limitation to the formation of novel radiopharmaceutical products is the tendency towards formation of Tc=0 species, but in addition formation of Tc$^{4+}$ or Tc$^{5+}$ complexes also limits the number and/or type of ligands prone to bind to the metal.

PCT Application WO 85/03063 describes the synthesis of the Tc≡N moiety as an intermediate in the preparation of radiopharmaceuticals by virtue of its ability to undergo various ligand substitution reactions. The Tc≡N core is again primarily based on the +5 oxidation state of Tc.

The reaction of TcCl$_6^{2-}$ with hydroxylamine salts under a variety of conditions to form a variety of complexes containing the Tc—NO moiety has been described (Eakins, JCS (1963) 6012; Radnovich and Hoard, J. Phys. Chem. 88 (26) (1984) 6713; Armstrong and Taube, Inorg. Chem. (1976) 15 (3), 1904). This literature is concerned with $^{99}$Tc and not with its metastable isotope $^{99m}$Tc. $^{99}$Tc has a half-life of 2.1×10$^5$ years, decays by emitting beta particles, and is of no interest as a radiopharmaceutical.

European Patent Application No. 0 291 281A describes technetium complexes containing the $^{99m}$Tc—NO moiety, together with a ligand which confers biological target-seeking properties on the complex, and their use as radiopharmaceuticals. The complexes are made from pertechnetate (TcO$_4^-$) by a variety of routes involving hydroxylamine salts. Studies of the coordination chemistry of technetium have generally been directed towards the synthesis and development of new $^{99m}$Tc labelled radiopharmaceuticals.[1] The majority of the technetium containing radiopharmaceuticals currently in clinical use involve technetium complexes containing either a mono-oxo or di-oxo core, i.e. [Tc$^V$=O]$^{3+}$ or [Tc$^V$O$_2$] respectively.[1,2] Technetium (V) oxo-species are used to image kidney, liver, brain and The terminal imido (2–) moiety, =NR, is formally isoelectronic to a terminal oxo (2–) function, =O. Many transition metal complexes containing an organo-imido ligand are known[3]. Examples include the following complexes based on rhenium[4,5,6] (I, II), tungsten[7] (III), vanadium[8] (IV) and molybdenum[9] (V):

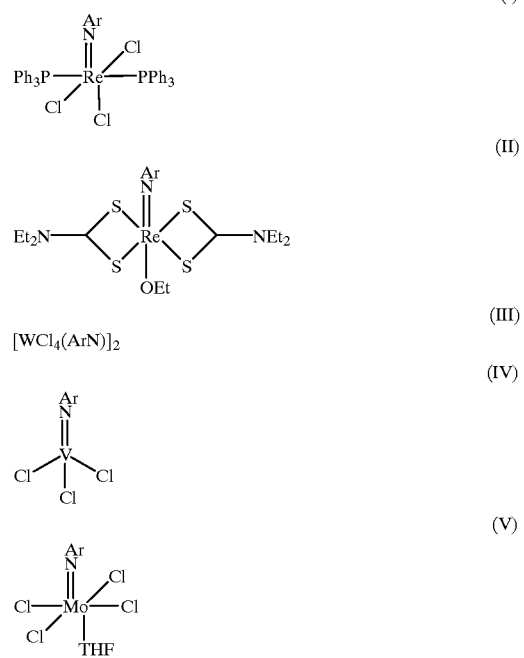

where Ar is an aryl group.

When the R substituent of a terminal imide ligand is a dialkyl amide moiety, NY$_2$, the imide ligand is more often described as a hydrazide (2–) ligand. Thus the terminal hydrazido (2–) moiety, =N—NR$_2$, is also isoelectronic to a terminal oxo (2–) function, and many transition metal complexes containing hydrazido (2–) ligands are known[10]. Examples of isostructural metal-oxo and metal-hydrazido (2–) complexes include the following[11,12,13,14]:

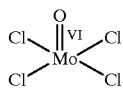

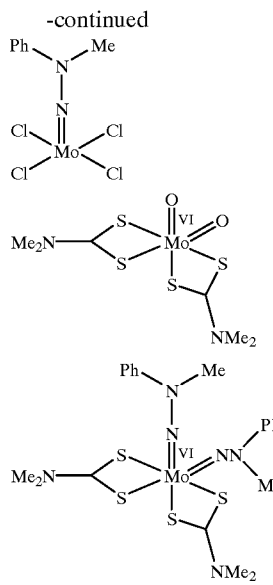

Similarly, the diazenido moiety, —N=NR, is isoelectronic and isostructural with the nitrosyl ligand (—NO).

Unlike oxo- and nitrosyl ligands, however, imide (2−), hydrazido (2−) and diazenido ligands can carry a variety of different substituents on the nitrogen atom which is not bound to the metal atom. The presence of any of these three moieties in a technetium complex therefore permits the preparation of new radiopharmaceuticals with a variety of biological characteristics which can be modulated by varying or altering the R substituents. In addition, the methods for the synthesis of complexes containing Tc=NR, Tc=N—NY$_2$ or Tc—N=NY moieties are compatible with the concomitant ligation of a wide variety of other ligands. It is this discovery which forms the basis of the present invention.

According to this invention there is provided a complex of technetium ($^{99}$Tc or $^{99m}$Tc) which contains the moiety Tc=NR, Tc—N=NY or Tc(—N=NY)$_2$, and a ligand which confers biological target-seeking properties on the complex, wherein R represents an aryl group, a substituted or unsubstituted alkyl group, or the grouping =NR$^1$R$^2$;

Y represents an aryl group or a substituted or unsubstituted alkyl group;

and R$^1$ and R$^2$ are hydrogen, aryl groups or substituted or unsubstituted aliphatic or cyclic alkyl groups, and may be both the same or different, provided that both are not hydrogen.

The complex is useful as a radiopharmaceutical.

Complexes in accordance with this invention have the formulae:

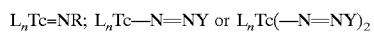

wherein L represents a mono- or multi-dentate ligand;
n is 1, 2, 3 or 4
and R and Y are as defined above.

The alkyl group substituents may be aliphatic (straight chain or branched) or cyclic, and may be substituted with, for example, oxygen, nitrogen, sulphur and/or phosphorus.

A wide range of ligands for these complexes are envisaged, including:

a) Phosphines and arsines of the general formula Q$_2$B(CD$_2$)$_n$BQ$_2$, where B is P or As; Q is H or aryl or substituted or unsubstituted alkyl, preferably C1–C4 alkyl or phenyl; n is 1, 2, 3 or 4; and (CD$_2$) is a substituted or unsubstituted methylene group. Related compounds are described in:

U.S. Pat. No. 4,481,184, U.S. Pat. No. 4,387,087, U.S. Pat. No. 4,489,054, U.S. Pat. No. 4,374,821, U.S. Pat. No. 4,451,450, U.S. Pat. No. 4,526,776, EP-A-0266910 (Amersham International; methylene bridged diphosphine complexes), EP-A-0311352 (Amersham International; phosphines containing ether groups), and ligands of general type

where B is P or As,
W is NR, S, Se, O, P or As,
R$^3$ is H or hydrocarbon such as C1–C6 alkyl or aryl,
m is 1 or 2, and
n is 1, 2, 3 or 4.

b) Methylene Diphosphonate (MDP)
c) Thiourea (TU)
d) Thiomalate (TMA)
e) Dimercaptosuccinic acid (DMSA)
f) Gluconate (GLUC)
g) Ethane-1-hydroxy-1,1-diphosphonate (EHDP)
h) Diethylene triamine pentaacetic acid (DTPA)
i) N-(2,6-[Dialkyl]phenyl carbamoylmethyl) iminodiacetate
   alkyl=Methyl (HIDA)
   Ethyl (EHIDA)
   Propyl (PIPIDA)
j) Dialkyl dithiocarbamate
k) Isonitriles of the general type C≡NR$^4$
   R$^4$=alkyl, alkoxy, ether
l) BAT Derivatives—of the general type illustrated below, and specifically:
   i) R$^5$=R$^{11}$=H
      R$^{6,7,9,10}$=Et
      R$^8$=N-methylspiropiperidinyl
   ii) R$^5$=R$^{11}$=H
      R$^{6,7,9,10}$=Et
      R$^8$=N-ethylspiropiperidinyl
   iii) R$^5$=R$^{11}$=H
      R$^{6,7,9,10}$=Et
      R$^8$=N-isopropylspiropiperidinyl

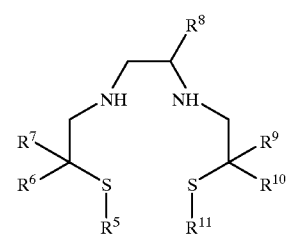

m) phenanthroline,
n) pentane-2,4-dione,
o) bipyridyl,
p) Other ligands having propylene amine oxime backbone of the general structural types described in EPA 123504 and 194843:

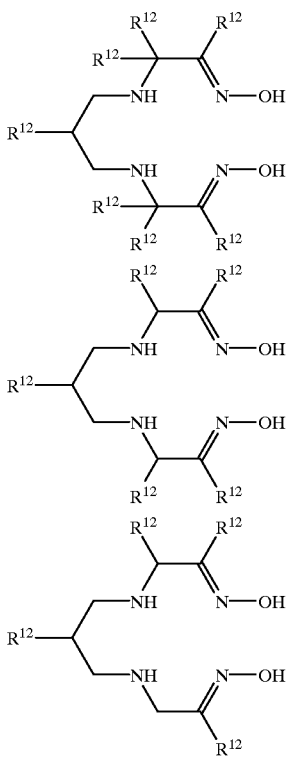

q) Bisthiosemicarbazones of the formula:

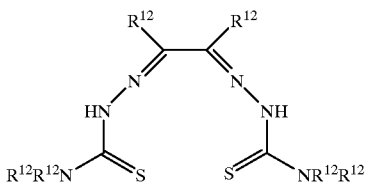

where the various groups $R^{12}$ can be the same or different and are H and/or alkyl and/or aryl substituents. Other suitable ligands are shown in Table 1.

The invention further provides methods for the preparation of the aforementioned complexes of technetium. One such method involves the derivatisation of technetium oxo-containing species by condensation with hydrazines or amines (equation A), isocyanates (equation B), sulphinylamines (equation C) or phosphinimines (equation D):

A: $L_nTc=O+H_2NR \rightarrow L_nTc=NR+H_2O$

B: $L_nTc=O+OCNR \rightarrow L_nTc=NR+CO_2$

C: $L_nTc=O+OSNR \rightarrow L_nTc=NR+SO_2$

D: $L_nTc=O+Ph_3P=NR \rightarrow L_nTc=NR+Ph_3P=O$ wherein R, L and n are defined as above.

The Driving force for these reactions is the formation of a stable product containing the former oxo function (i.e. water, carbon dioxide, sulphur dioxide or phosphine oxide), which is generally easily removed after the oxo group transfer, leaving the desired technetium hydrazido (2−) or imido complex.

An alternative method of preparation involves the reaction of hydrazines (equation E) or amines (either aliphatic or aromatic) (equation F) with complexes containing technetium-halogen bonds:

E: $L_nTc\ Cl_2+H_2NNR^1R^2 \rightarrow L_nTc=NNR^1R^2+2HCl$

F: $L_nTc\ Cl_2+H_2NR \rightarrow L_nTc=NR+2HCl$ where L, R, $R^1$ and $R^2$ are as previously defined.

The driving force for these reactions is the concomitant formation of the volatile, easily removed hydrogen halide during the metathesis reaction.

It will be appreciated that the hydrazides and diazenides can be considered as essentially being functionalised imide ligands. The hydrazide (2−) ligand, $=NNR^1R^2$, is just the imide ligand, $=NR$, where R is $NR^1R^2$; and the diazenide ligand results when R is hydrogen. In this case, the intermediate hydrazide (2−) complex is deprotonated by a base to give a metal-diazenide complex with concomitant reduction of the metal centre:

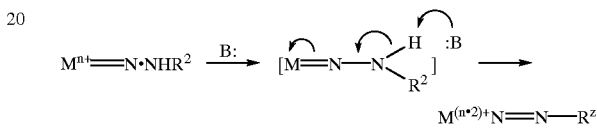

In the reactions reported herein, the base is always the added excess of hydrazine in the solution.

Turning now to the preparation of the technetium complexes containing an imido moiety, the approach has been to replace the oxo function in $[TcOX_4]^-$ (X=Cl, Br) using arylisocyanates (reaction type equation B). This formed a convenient entry point into the work by extending an established route for the synthesis of Tc=NR complexes. This method has only been previously used for generation of neutral imido products from neutral transition metal oxo starting materials.[17] The work reported here is thus the first example of the method extended to the preparation of anionic transition metal imido complexes, and also to technetium chemistry.

Reaction of $[Tc^VOX_4]^-$ with excess ArNCO in refluxing dry toluene under nitrogen gives excellent yields of the desired $Tc^V$-imido products isolated as solids on ether trituration of the residue obtained directly from the reaction mixture (equation G):

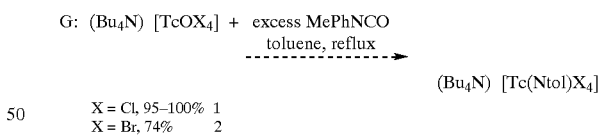

X = Cl, 95–100%  1
X = Br, 74%  2

Even though the method gives good yields of reasonably pure solids, the reaction is not trivial. The starting isocyanates are quite moisture and air sensitive such that the reaction must be strictly performed under an atmosphere of $N_2$. 1 and 2 are black-blue solids that are also quite sensitive to adventitious moisture, however, they are stable under dry $N_2$. That the products are very sensitive to moisture is evidenced by the fact that if reagent grade diethyl ether is used in the trituration phase of the workup procedure instead of anhydrous ether, then the product is isolated as a red-brown insoluble polymeric compound. The products also do not always chromatograph (HPLC) satisfactorily.

The products $[Tc(Ntol)X_4]^-$ contain the new core moiety $[Tc^V=NR]^{3+}$ which is formally analogous to the well known $[Tc=O]^{3+}$ core[1]. $[Tc(NR)X_4]^-$ is a sixteen electron species in which the imido ligand functions as a four electron donor; the technetium-nitrogen bond is therefore expected to be a short, linear multiple [Tc≡NR] bond. Attempted structural characterisation of [Tc(Ntol)Cl$_4$]$^-$ as its PPh$_4$$^+$ salt by X-ray crystallography has so far been unsuccessful due to its sensitive nature. The products 1 and 2 are very good starting materials for the preparation of many new Tc≡NR complexes.

In view of the somewhat sensitive nature of 1 and 2, investigation of much more stable Tc-imido complexes was undertaken. The direct metathesis reactions of [TcOCl$_4$]$^-$ with aromatic amines was undertaken in the presence of phosphine ligands. Reactions of this type may show promise in $^{99m}$Tc chemistry in view of the wide variety of substituted aromatic amines available commercially.

Reaction of [TcOCl$_4$]$^-$ with ArNH$_2$ in refluxing MeOH in the presence of the monodentate phosphine PPh$_3$ gives the green-brown neutral Tc imido complexes which analyse for [Tc(NR)Cl$_3$(PPh$_3$)$_2$] (equation H):

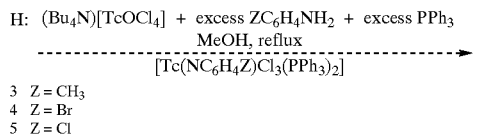

3  Z = CH$_3$
4  Z = Br
5  Z = Cl

Chromatographic analysis (HPLC, beta detection) of these products show only one significant $^{99}$Tc-containing species. These neutral Tc$^V$ complexes also contain the new [Tc$^V$≡NR]$^{3+}$ core. They are diamagnetic, air-stable solids which are very soluble in CH$_2$Cl$_2$, CHCl$_3$, moderately soluble in alcohols, and insoluble in ether and petrol. They exhibit a singlet (ca. 30 ppm) in the $^{31}$P NMR spectrum, indicating two trans-PPh$_3$ groups in identical environments. Structural characterisation of 3 by X-ray has now been carried out and FIG. 1 gives a Ball and Stick representation of the complex molecule. The diagram shows a linear tolylimide group and the two PPh$_3$ groups to be trans. The [Tc≡Ntol] unit in 3 may therefore be correctly assigned as a linear four electron donor imido ligand, and the complex is formally an 18-electron species.

This work therefore represents the first structurally characterised Tc$^V$-imido complex.

The [Tc(NR)Cl$_3$(PPh$_3$)$_2$] compounds are much superior starting materials than [TC(NR)X$_4$]$^-$ because these are much more stable Tc=NR species.

Reaction of [TcOCl$_4$]$^-$ with excess amine and dppe in refluxing MeOH or EtOH allows the isolation of good yields of the cationic Tc-imido complexes

[Tc$^{IV}$(NC$_6$H$_4$Z)Cl—(dppe)$_2$]+ as their BPh$_4$$^x$ salts (equation I):

I:  (Bu$_4$N)[TcOCl$_4$] + excess ZC$_6$H$_4$NH$_2$ + excess dppe ---->

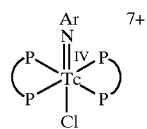

6  Z = CH$_3$, 60%, violet
7  Z = Br, 64%, maroon
8  Z = Cl, 64%, maroon

These complexes 6, 7, and 8 are all air-stable darkly coloured cationic Tc$^{IV}$-imido complexes. Chromatographic analysis (HPLC, beta detection) indicates single $^{99}$Tc-containing species. They are quite soluble in CH$_2$Cl$_2$ and insoluble in ether, petrol and alcohols. They may be conveniently recrystallised from CH$_2$Cl$_2$/MeOH.

Their assignment as Tc(IV) complexes is from the following characterization: The analysis stoichiometry fits the formula [Tc(NR)Cl(dppe)$_2$](BPh$_4$). Although γ Tc=N is not assignable there is no evidence for γ NH in the infrared. The compounds exhibit very broadened NMR spectra ($^1$H, $^{31}$P) at room temperature which are not easily assigned. They are assumed to be paramagnetic Tc$^{IV}$imido complexes and not Tc$^{III}$-amido (TcNHR) complexes on this basis.

This represents another new core, the [Tc$^{IV}$=NR]$^{2+}$ moiety. Evidence for the existence of this new Tc$^{IV}$ core comes from the structural characterisation of a [Tc$^{IV}$-hydrazido(2-) bis(dppe)Cl]$^+$ cation which contains a [Tc$^{IV}$NNR$_2$]$^{2+}$ core$^{18}$. Hydrazido(2-) and imido(2-) are formally analogous. Further evidence comes from the existence and relative stability of the analogous [Tc$^{IV}$=O]$^{2+}$ core from the electrochemical reduction of some Tc oxo Schiff base complexes.

It is to be understood that reactions of the aforementioned type A–F are well known for the synthesis of various transition metal hydrazido (2-) and imido complexes$^{3,10}$. While it is believed that they have not previously been used for the production of technetium complexes of the kind described and claimed herein, it is acknowledged that the synthesis of technetium-nitride complexes using hydrazine hydrochloride itself has already been reported$^{15,16}$.

Using the approach of equation A above, the reactions of hydrazines with [NBu$_4$] [TcOCl$_4$] were studied, and the intermediate products further functionalised with mono- or bi-dentate ligands. In particular, the reaction of complexes containing technetium-oxo moieties [Tc=O] with mono-substituted hydrazines or 1,1-disubstituted hydrazines produces technetium-diazenide or technetium-hydrazide (2-) species.

The facile synthesis of [cCl(NNPh)$_2$(PPh$_3$)$_2$] from [Bu$_4$Nt][TcOCl$_4$], PhNHNH$_2$, and PPh$_3$ in methanol under reflux has been demonstrated.$^{25}$ This complex proved to be somewhat insoluble and could not be satisfactorily recrystallised due to its poor solubility. This unsubstituted phenyl-diazenido-complex thus appears to be polymeric, possibly containing chloro-bridges. Consequently it was not thought to be a suitable starting material for investigation of substitution chemistry.

Use of 4-substituted hydrazine hydrochlorides 4-XC$_6$H$_4$NHNH$_2$.HCl(X=Cl, CH$_3$) has lead to the preparation of the analogous bisdiazenido-complexes [TcCl(NNC$_6$H$_4$X)$_2$(PPh$_3$)$_2$] (X=Cl, 9; X=CH$_3$, 10) These air-stable orange crystalline solids are reasonably soluble compounds and are much superior starting materials. Complex 9 (X=Cl) in particular has proved to be the most suitable for a systematic investigation of the substitution chemistry of the technetium bis diazenido-complexes, giving relatively clean products on reaction with the appropriate ligand.

A most important development in this work is the fact that these diazenido-complexes [TcCl(NNR)$_2$(PPh$_3$)$_2$] may also be synthesised directly from [TcO$_4$]$^-$. Reaction of [NH$_4$][TcO$_4$] with ClC$_6$H$_4$NHNH$_2$.HCl and PPh$_3$ in dry methanol under reflux gives a good (60–70%) yield of [TcCl(NNC$_6$H$_4$Cl)$_2$(PPh$_3$)$_2$]9 Many variations in experimental conditions were tried. The best method is reported here. This result suggests that all technetium diazenido-complexes may be synthesised in good yield directly from [TcO$_4$]$^-$.

In order to investigate which complexes could be synthesised directly from [TcO$_4$]$^-$ in future work, it has been important to demonstrate that the diazenido- (and imido-) cores may be incorporated into a wide variety of complex types. For diazenido-cores this has mainly been approached by the systematic substitution of 9.

Reaction of 9 with excess dppe in methanol under reflux gives pure [TcCl(NNC$_6$H$_4$Cl)(dppe)$_2$]$^+$, 12 isolated as orange crystalline BPh$_4^-$ or PF$_6^-$ salts in good yield. Complexes of this type may also be prepared directly from [NH$_4$][TcO$_4$].

Reaction of 9 with dmpe under similar conditions leads to the isolation of a pale-pink cationic solid (HPLC retention time 10 minutes, single species) containing no nitrogen. This product could not be isolated in pure form, but is tentatively formulated as [Tc$^I$(dmpe)$_3$][BPh$_4$]. The analogous reaction under less forcing conditions at room temperature leads to the desired cation [TcCl(NNC$_6$H$_4$Cl)(dmpe)$_2$]$^+$ isolated as its PF$_6^-$ salt (HPLC retention time 9.6 minutes, single species).

In order to elucidate the validity of both [Tc(N$_2$Ar)$_2$]$^+$ and [Tc(N$_2$Ar)]$^{2+}$ as new cores for the development of Tc-based radiopharmaceutical products it was necessary to investigate the lability of the —N$_2$Ar unit on reaction with other ligands. Detailed HPLC experiments (beta detection) were performed to see if a bis diazenido-intermediate was formed in the preparation of the cation 12 (retention time 14 minutes) from the starting material 9 (retention time 9.4 minutes). The HPLC results showed that the cation formed after only 15 minutes stirring at room temperature, and that no other Tc-containing intermediate was detected. This proves that one —N$_2$Ar moiety is very labile, and is easily lost in solution at room temperature in the presence of the appropriate ligand to give the monodiazenido-product.

Reaction of 9 and 10 with the less bulky phosphines (PMe$_2$Ph, PMePh$_2$) gave single species in solution (HPLC). However, the high solubility precluded further workup of these apparently cationic products. Reaction of [Bu$_4$N] [TcOCl$_4$], XC$_6$H$_4$NHNH$_2$.HCl (X=Cl, CH$_3$) and the appropriate phosphine also leads to isolation of these solutions (HPLC).

Reaction of the commercially available hydrazine O$_2$NC$_6$H$_4$NHNH$_2$ with [Bu$_4$N] [TcOCl$_4$] and PPh$_3$ in methanol leads to the isolation of the lime-green Tc(III) monodiazenido-complex [TcCl$_2$(NNC$_6$H$_4$NO$_2$)(PPh$_3$)$_2$], 11 in reasonable yield. Apparently a bis diazenido-complex is not formed from reaction of this nitro-substituted phenylhydrazine. The complex 11 promises to be a useful starting material for the preparation of a variety of monodiazenido-complexes as it has two easily replaceable chlorides. In the presence of dppe in methanol-toluene under reflux complex 11 gives orange [TcCl(NNC$_6$H$_4$NO$_2$)(dppe)$_2$]$^+$, 13 isolated as its BPh$_4$-salt in good yield. [TcCl(NNC$_6$H$_4$NO$_2$)(dmpe)$_2$][PF$_6$] (retention time 10 minutes, single species) was prepared in high yield directly from [TcOCl$_4$]$^-$, the hydrazine, and dmpe in refluxing methanol-toluene.

Reaction of 9 with sodium dimethyldithiocarbamate in absolute ethanol under reflux gives the novel orange Tc(III) diazenido-complex [Tc(NNC$_6$H$_4$Cl) (S$_2$CNMe$_2$)$_2$(PPh$_3$)], 14 in reasonable (66%) yield. Complex 14 is air-stable both in the solid state and in solution. Recrystallisation from CH$_2$Cl$_2$/Et$_2$O gives X-ray quality orange crystals. Satisfactory elemental analysis and spectroscopic data suggest the formulation to be correct. The room temperature $^1$H NMR spectrum of 14 is indicative of its coordination geometry. The four methyl groups in 14 appear as four sharp singlets. This resonance pattern shows that the two dithiocarbamato ligands are non-equivalent, and is consistent with a cis-conformation. This has to be confirmed by X-ray structure analysis. If the dithiocarbamato ligands were trans- and the four methyl groups thus equivalent, the $^1$H spectrum would show a single resonance which would not be expected to change with temperature.

Reaction of 9 with maltol gives a dark-orange crystalline compound. This is a single species (HPLC) and analyses as [TcCl(NNC$_6$H$_4$Cl)(maltol) (PPh$_3$)$_2$], 15. This novel Tc(III) diazenido complex is formally analogous to the structurally characterised [ReCl(NNCOPh)(maltol)(PPh$_3$)$_2$]$^{26}$, and is the first reported Tc complex containing the maltol ligand.

Reaction of 9 with the tetradentate N$_2$O$_2$(2−) ligand salenH$_2$ in methanol-toluene under reflux in the presence of Et$_3$N gives the neutral dark-green Tc(III) diazenido-complex [Tc(NNC$_6$H$_4$Cl)(salen)(PPh$_3$)], 16 in good yield. Similar reaction of 9 with the obligately planar tetradentate N$_2$O$_2$ (2−) ligand salphenH$_2$ gave no well defined product suggesting that a cis-geometry of the —N$_2$Ar and PPh$_3$ groups is preferred. Further evidence for a preferred cis-geometry is suggested from the spectroscopic results of 14. This is expected to be confirmed by X-ray structure analysis.

Reaction of 9 with the N$_2$S$_2$ ligand (HSCH(Me) CONHCH$_2$—)$_2$ in the presence of Et$_3$N gave a dark-brown solid. The product was too insoluble for satisfactory analysis by NMR, but appeared to be diamagnetic. Elemental analysis on the product isolated directly from the reaction mixture suggested the formulation as a bis diazenido-complex

17.

Much effort has been directed to the development of a synthetic route to Tc imido-complexes directly from [TcO$_4$]$^-$ Reaction of aqueous methanolic solutions of [TcO$_4$]$^-$ with aromatic amine and PPh$_3$ in the presence of concentrated HCl gives only low yields of the desired Tc(V) imido-complexes [TcCl$_3$(NAr)(PPh$_3$)$_2$]. These complexes have been prepared previously from [Bu$_4$N][TcOCl$_4$].$^{25}$ The nature of the reaction from [TcO$_4$] appears to be very dependent on the concentration of HCl used. Use of excess HCl gives [TcCl$_4$ (PPh$_3$)$^2$].

The use of amine hydrochloride (ArNH$_3$Cl) as an alternative to the addition of HCl in this reaction has also been investigated in some detail. [TcO$_4$]$^-$ reacts with ArNH$_3$Cl and PPh$_3$ in aqueous methanol to give a bright blue, neutral product in high yield after about 20 minutes stirring at room temperature. This product appears to be independent of the aromatic amine hydrochloride used. The blue compound appears to be diamagnetic (NMR) and shows evidence for coordinated PPh$_3$, but contains no nitrogen. This compound analyses reasonably as [Tc$_2$Cl$_4$(PPh$_3$)$_4$] which is analogous to many known Re-Re multiply bonded species. Use of aliphatic amine hydrochlorides (RNH$_3$Cl) leads to rapid conversion to black insoluble "TcO$_2$. xH$_2$O".

Reaction of [NH$_4$][TcO$_4$] with the hydrochloride of anthranilic acid (2-HO$_2$CC$_6$H$_4$NH$_3$Cl) under analogous conditions gives a lime-green precipitate. This analyses reasonably well as [TcCl$_2$(NC$_6$H$_4$ CO$_2$)(PPh$_3$)$_2$], 18 and is expected to have the novel structure containing a bent TcNC framework. The bent chelating imidobenzoate(3−) ligand is thus a new core moiety for technetium. The complex 18 may also be prepared from [TcOCl$_4$]$^-$ in lower yield. Anthranilic acid is known to react with [ReOCl$_3$(PPh$_3$)$_2$] in ethanol to give the chelating imidobenzoate(3−) complex [ReCl(OEt) (NC$_6$H$_4$CO$_2$)(PPh$_3$).$^{27}$

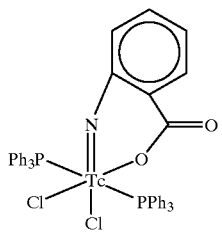

This is a major development as it suggests that imido-complexes are more generally accessible from [TcO$_4$]$^-$. The chelate effect must in some way stabilise the formation of this imido-ligand. The establishment of a conjugation pathway through the M=N, C=C, and C=O may be a driving force for its formation. The reaction of [TcO$_4$]$^-$ and anthranilic acid hydrochoride in the presence of a wide variety of non-phosphine ligands is envisaged.

Much effort has been directed to synthesis of Tc imido-ligands from [TcO$_4$]$^-$ using the hydrazines RCONHNHAr (R=CH$_3$, Ph), and also their hydrochlorides as a source of the NAr ligand. Use of the symmetrically substituted hydrazines RNHHNR (R=Me, Et, PhCO, Ph) is also envisaged. Preliminary experiments for both [TcO$_4$]$^-$ and [TcOCl$_4$]$^-$ have shown that mixtures of products are being formed (HPLC).

Our work has resulted in the synthesis of two new classes of technetium complexes with hydrazido (2−), i.e. =NNR$_2$, and diazenido, i.e. —NNR, substituents, at both the carrier added ($^{99}$Tc) and the no carrier added ($^{99m}$Tc) levels. Both neutral and cationic derivatives have been prepared within each class. These complexes are useful as radiopharmaceuticals and thus provide a new range of such reagents.

Specifically, the following new complexes containing hydrazido (2−) and diazenido moieties have been prepared:

---

$^{99}$Tc: Carrier Added Level
  [Tc$^V$(NNMePh)Cl$_3$(PPh$_3$)$_2$]
  [Tc$^V$(NNMePh)Cl$_2$(PMe$_2$Ph)$_3$][PF$_6$]
  [Tc$^V$(NNMePh)Cl(Et$_2$NCS$_2$)$_2$]
  [Tc(N$_2$)Cl(dppe)$_2$]
  [Tc$^{IV}$(NNMe$_2$)Cl(dppe)$_2$][PF$_6$]
  [Tc$^V$O(NH)dppe][PF$_6$]
  [Tc$^{III}$(NNPh)$_2$Cl(PPh$_3$)$_2$]
  [Tc$^{III}$(NNPh)Cl(dppe)$_2$][PF$_6$]
  [Tc(NNC$_6$H$_4$Cl)Cl(dppe)$_2$][PF$_6$]
  [Bu$_4$N][Tc(NC$_6$H$_4$CH$_3$)Br$_4$],
  [Bu$_4$N][Tc(NC$_6$H$_4$CH$_3$)Cl$_4$], Tc
  (NC$_6$H$_4$Z)Cl$_3$(PPh$_3$)$_2$ where Z = CH$_3$, Br, Cl,
  [Tc(NC$_6$H$_4$Z)Cl(dppe)$_2$][BPh$_4$], where Z is as above.
$^{99m}$Tc: No-Carrier Added Level*
  [Tc$^{III}$(NNPh)Cl(L)$_2$]$^+$
  L = dmpe, dppe, P46, P53, P56, P68, PL28, PL31,
    PL34, PL37, PL38, PL40, PL42, PL43, PL46,
    PL49, PL50.
  [Tc$^{III}$(NNC$_6$H$_4$NO$_2$)Cl(L)$_2$]$^+$
  L = dmpe
  [Tc$^{IV}$(NNMePh)Cl(L)$_2$]$^+$
  L = dmpe, P34, P46, P53, P65, P68, PL28, PL38

*The structures of the ligands, L, given here are shown in Table 1.

Of these, animal biodistribution data has been obtained for the following $^{99m}$Tc species and the results are shown in Tables 2, 3 and 4:

TABLE 2

[Tc$^{III}$(NNPh)Cl(L)$_2$]$^+$
L = dmpe, PL28, P46, PL42, PL43, P65, PL50, PL38

TABLE 3

[Tc$^{III}$(NNC$_6$H$_4$NO$_2$)Cl(L)$_2$]$^+$
L = dmpe

TABLE 4

[Tc$^{IV}$(NNMePh)Cl(L)$_2$]$^+$
L = dmpe, P46, P65

This invention will now be further illustrated by the following Examples:

$^{99}$Tc Complexes

All reactions were performed under an atmosphere of nitrogen using predried, distilletd solvents unless noted otherwise. [NBu$_4$][TcOCl] was prepared by the literature procedure[20]. All other reagents used were obtained from commercial sources and used as received. Aqueous solutions of [NH$_4$][TcO$_4$] were obtained from Amersham International plc.

All complexes were characterised by elemental analysis, IR, $^1$H NMR and $^{31}$p NMR. Only analytical data are included here but spectroscopic information is available. In addition to the above physical characterisation of the complexes single crystal X-ray structures have been obtained for four complexes: [Tc(NNPh)Cl(dppe)$_2$][PF$_6$], [Tc(NH)O(dppe)$_2$][PF$_6$], [Tc(NNMe$_2$)Cl(dppe)$_2$][PF$_6$] and Tc(NC$_6$H$_4$CH$_3$)C$_3$ (PPh$_3$)$_2$.

EXAMPLE 1

Reaction of (Bu$_4$N)[TcOX$_4$] (X=Cl, Br) with 4-Tolyl-isocyanate i) Tetrabutylammonium(1+)tetrachloro(p-tolylimido) technetate (V) (1−), (Bu$_4$N)[Tc(Ntol)Cl$_4$]1

(Bu$_4$N)[TcOCl$_4$](0.194 g, 0.39 mmol) was suspended in dry degassed toluene (10 ml) and MePhNCO (0.25 ml, 1.98 mmol, 5 equivalents) was added. The mixture was then vigorously refluxed under N$_2$ for 45 minutes. After cooling to room temperature the toluene was decanted off, and the black residue was triturated with dry diethyl ether (10 ml) before collection of the blue-black solid 1 by filtration. On washing thoroughly with diethyl ether the product was dried in vacuo. (Yield 0.229 g, 0.39 mmol, 100%). In similar preparations of 1 the yield was never less than 95% and therefore the conversion was considered to be essentially quantitative. (Found: C,49.31; H,7.22; N,5.02. calc for TcC$_{23}$H$_{43}$N$_2$Cl$_4$: C,47.03; H,7.37; N,4.77%); $^1$H NMR (d$_6$-DMSO) 0.9[12H, broad unresolved triplet, (CH$_3$(CH$_2$)$_3$)$_4$N]; 1.4[24H, broad multiplet, (CH$_3$(CH$_2$)$_3$)$_4$N]; 2.2[3H, singlet, CH$_3$C$_6$H$_4$N—Tc]; 7.0–7.414H, multiplet, CH$_3$C$_6$H$_4$NTc]; v$_{max.}$ (Nujol mull, KBr plates) 1170 m br cm (Tc=N, tentative assignment).

ii) Tetrabutylammonium(1+)tetrabromo(p-tolylimido) technetate (V) (1−), (Bu$_4$N)[Tc(Ntol)Br$_4$] 2

The blue-black product 2 was prepared in a similar fashion to 1 using (Bu$_4$N) [TcOBr$_4$] (0.268 g, 0.396 mmol) and MePhNCO (0.25 ml, 1.98 mmol, 5 equivalents) in refluxing dry toluene (15 ml). (Yield 0.224 g, 0.29 mmol, 74%). HPLC retention time 9.6 minutes, single species; (Found: C,36.73; H,6.43; N,3.16. calc for TcC$_{23}$H43N$_2$Br$_4$:

C,36.10; H,5.66; N,3.66%); $^1$H NMR (CDCl$_3$) 1.0[12H, broad unresolved triplet, (CH$_3$(CH$_2$)$_3$)$_4$N]; 1.5[24H, broad multiplet, (CH$_3$(CH$_2$)$_3$)$_4$N]; 2.27[3H, singlet, CH$_3$C$_6$H$_4$NTc]; 6.9–7.5[4H, multiplet, CH$_3$C$_6$H$_4$NTc]; ν$_{max.}$ (Nujol mull, KBr plates) 1175 cm$^{-1}$ (Tc=N, tentative assignment).

EXAMPLE 2
Reactions of (BU$_4$N)[TcOCl$_4$] with Aromatic Amines (4-ZC$_6$H$_4$NH$_2$Z=CH$_3$, Br, Cl) in the Presence of Triphenylphosphine, PPh$_3$ i) Trichloro(p-tolylimido)bis(triphenylphosphine) technetium (V), TC(NC$_6$H$_4$Z)Cl$_3$(PPh$_3$)$_2$Z=CH$_3$, 3

(Bu$_4$N)[TcOCl$_4$](0.216 g, 0.43 mmol), CH$_3$C$_6$H$_4$NH$_2$ (0.07 g, 0.65 mmol, 1.5 equivalents) and PPh$_3$ (0.34 g, 1.3 mmol, 3 equivalents) were refluxed in dry methanol (10 ml) under N$_2$ for 40 minutes. After cooling to room temperature, the brown-green mixture was evaporated to 5 ml, and diethyl ether (15 ml) was added to aid precipitation of 3. The green-brown product was collected by filtration, washed thoroughly with ether and dried. The product could be recrystallised from CH$_2$Cl$_2$/hexane mixture. (Yield 0.094 g, 0.11 mmol, 26%). HPLC retention time 10.8 minutes, single species; (Found: C,59.01; H,4.35; N,1.76; Cl,12.80. calc for TcC$_{43}$H$_{37}$NCl$_3$P$_2$: C,61.84; H,4.46; N,1.68; Cl,12.74%); $^1$H NMR (CDCl$_3$) 2.2[3H, s, CH$_3$C$_6$H$_4$NTc]; 6.5–6.8[4H, m, CH$_3$C$_6$ H$_4$NTc]; 7.0–8.0[30H, m, phenyl H]. There was no evidence of NH in the proton spectrum; 31P—[$^1$H]NMR (CDCl$_3$) 30.02 s ppm; ν$_{max}$ (Nujol mull, KBr plates) 1165 cm (Tc=N, tentative assignment). There were no absorptions which could be attributed to 'NH.

ii) Trichloro(p-bromophenylimido)bis(triphenylphosphine) technetium (V), Tc(NC$_6$H$_4$Z)Cl$_3$(PPh$_3$)$_2$Z=Br, 4

(Bu$_4$N) [TcOCl$_4$] (0.210 g, 0.42 mmol), BrC$_6$H$_4$NH$_2$ (0.11 g, 0.64 mmol, 1.5 equivalents) and PPh$_3$ (0.331 g, 1.26 mmol, 3 equivalents) were refluxed in dry methanol (10 ml) to give on workup and recrystallisation from CH$_2$Cl$_2$/hexane a very low yield of brown solid 4. (Yield 0.052 g, 0.06 mmol, 14%). HPLC retention time 9.6 minutes, single species; (Found: C,54.38; H,4.00; N,1.53; Cl,10.56. calc for TcC$_{42}$H$_{34}$ NP$_2$Cl$_3$Br: C,56.05; H,3.81; H,1.56; Cl,11.82. calc for TcC$_{42}$H$_{34}$ NP$_2$C$_3$Br.½ CH$_2$Cl$_2$ C,54.45; H,3.72; N,1.48; Cl,14.95%); $^1$H NMR (CDCl$_3$) 5.25(s, CH$_2$Cl$_2$)]; 6.8[4H, m, BrC$_6$H$_4$NTc]; 7.0–8.0[30H, m, phenyl H]; $^-$P—[$^1$H] NMR (CDCl$_3$) 29.93 s ppm; ν$_{max.}$ (Nujol mull, KBr plates) 1165 cm$^{-1}$ (Tc=N, tentative assignment).

iii) Trichloro(p-chlorophenylimido)bis(triphenylphosphine) technetium (V), Tc(NC$_6$H$_4$Z)Cl$_3$(PPh$_3$)$_2$ Z=Cl, 5

(Bu$_4$N)[TcOCl$_4$] (0.272 g, 0.545 mmol), ClC$_6$H$_4$NH$_2$ (0.104 g, 0.82 mmol, 1.5 equivalents) and PPh$_3$ (0.43 g, 1.64 mmol, 3 equivalents) were refluxed in dry methanol (10 ml) to give a very low yield of brown solid 5. (Yield 0.084 g, 0.098 mmol, 18%). HPLC retention time 9.2 minutes, single species; (Found: C,55.85; H,3.86; N,1.63. calc for TcC$_{42}$H$_{34}$NP$_2$Cl$_4$: C,58.96; H,4.00; N,1.64%); $^1$H NMR (CDCl$_3$) 6.5–6.7[4H, m, ClC$_6$H$_4$NTc]; 7.0–8.0[30H, m, phenyl H]; $^{31}$ P—($^1$H) NMR (CDCl$_3$) 29.87 s ppm; ν$_{max.}$ (Nujol mull, KBr plates) 1170 cm$^{-1}$ (Tc=N, tentative assignment.

EXAMPLE 3
Reactions of (Bu$_4$N)[TcOCl$_4$) with Aromatic Amines (4-ZC$_6$H$_4$ NH$_2$, Z=CH Br, Cl) in the Presence of Bis (diphenylphosphino)ethane, dppe i) [Tc(NC$_6$H$_4$Z)Cl(dppe)$_2$](BPh$_4$) Z=CH$_3$, 6

(Bu$_4$N)[TcOCl$_4$] (0.333 g, 0.67 mmol), CH$_3$C$_6$H$_4$NH$_2$ (0.36 g, 3.33 mmol, 5 equivalents), and dppe (0.80 g, 2.0 mmol, 3 equivalents) in dry degassed methanol (20 ml) were refluxed for 1 hour. After cooling to room temperature, the violet mixture was filtered into a clean flask to remove some insoluble red material. Sodium tetraphenylborate (0.23 g, 0.67 mmol) in methanol (5 ml) was added with stirring to immediately precipitate out a copious amount of violet solid 6. The product was collected by filtration and washed thoroughly with MeOH, and then ether. The product could be recrystallised from CH$_2$Cl$_2$/MeOH or CH$_2$Cl$_2$/hexane. (Yield 0.544 g, 0.40 mmol, 60%). HPLC retention time 8.4 minutes, one major species; (Found: C,74.09; H,7.09; N,1.70; Cl,3.22. calc for TcC$_{83}$H$_{75}$NClP$_4$B: C,73.54; H,5.58; N,1.03; Cl,2.62%).

There are no infrared absorptions assignable to NH stretches, and the $^v$Tc=N stretch could not be assigned unambiguously. The product gave a broadened $^1$H NMR spectrum and was assumed to be paramagnetic Tc(IV). The $^{31}$P NMR spectrum also showed broadened resonances.

If less ArNH$_2$ was used in the reaction a red precipitate believed to be [Tc$^{III}$Cl$_2$(dppe)$_2$]Cl forms in approximately 50% yield from the MeOH on cooling to room temperature.

ii) (Tc(NC$_6$H$_4$Z)Cl(dppe)$_2$](BPh$_4$) Z=Br, 7

(Bu$_4$N)[TcOCl$_4$](0.179 g, 0.36 mmol), BrC$_6$H$_4$NH$_2$ (0.31 g, 1.79 mmol, 5 equivalents) and dppe (0.429 g, 1.08 mmol, 3 equivalents) were refluxed in dry methanol (10 ml, 1 hour). NaBPh$_4$ (0.122 g, 0.36 mmol) in MeOH (5 ml) was added to the cooled filtered reaction mixture with stirring to isolate 7 as a maroon solid on filtration. (Yield 0.325 g, 0.23 mmol, 64%). HPLC retention time 7.6 minutes, one major species. Analysis on the crude material gave (Found: C,73.19; H,5.91; N,0.89; Cl,3.19. calc for TcC$_{82}$H$_{72}$ NBrClP$_4$B: C,69.33; H,5.11; N,0.99; Cl,2.50%) and suggests contamination with BPh$_4^-$ or Cl$^-$. The product could be recrystallised from CH$_2$Cl$_2$/MeOH.

iii) [Tc(NC$_6$H$_4$Z)Cl(dppe)$_2$](BPh$_4$) Z=Cl, 8

(BU$_4$N)(TcOCl$_4$) (0.28 g, 0.56 mmol), ClC$_6$H$_4$NH$_2$ (0.358 g, 2.8 mmol, 5 equivalents) and dppe (0.67 g, 1.68 mmol, 3 equivalents) were refluxed in dry methanol (15 ml, 75 minutes). NaBPh$_4$ (0.19 g, 0.56 mmol) in MeOH (5 ml) was added to the cooled filtered reaction mixture with stirring to precipitate out the dark maroon solid 8 which was collected by filtration. (Yield 0.497 g, 0.36 mmol, 64%). HPLC retention time 8.0 minutes, one major species. Analysis on the crude material gave (Found: C,73.56; H,5.94; N,1.72; Cl,3.26. calc for TcC$_{82}$H$_{72}$NCl$_2$P$_4$B: C,71.57; H,5.27; N,1.02; Cl,5.15%) and suggests contamination with BPh$_4^-$. The product could be recrystallised from CH$_2$Cl$_2$/MeOH.

EXAMPLE 4
The preparation of [Tc(NNPh)$_2$Cl(PPh$_3$)$_2$]

Dry, distilled MeOH (5 cm$^3$) was added to a reaction flask containing a magnetic stirring bar, 222 mg PPh$_3$ (0.85 mmol) and 70 mg [NBu$_4$][TcOCl$_4$] (0.14 mmol). This gave an orange suspension containing undissolved PPh$_3$. After five minutes 0.60 cm$^3$ of PhNHNH$_2$ (6.1 mmol) was added and the reaction mixture was heated to reflux for one hour. The solution was cooled to room temperature overnight and the resultant yellow-gold precipitate was collected, washed with MeOH (5 cm 3) and Et$_2$O (10 cm$^3$). The yield of Tc(NNPh)$_2$Cl(PPh$_3$)$_2$, after drying in vacuo, was 94 mg (0.11 mmol, 80%) based on technetium. This material is only partially soluble in halogenated solvents and insoluble in alcohols. Hence, attempts to purify the complex were only partially successful. Analysis calculated for C$_{48}$H$_{40}$ClN$_4$P$_2$Tc: 66.32% C,4.64% H,6.45% N. Found: 64.23% C,4.28% H,4.87% N.

EXAMPLE 5
The preparation of [Tc(NNPh)Cl(dppe)$_2$][PF$_6$]
Method 1

52 µl of PhNHNH$_2$ (0.53 mmol) was added to a stirred solution of 80 mg [NBu$_4$][TcOCl$_4$] (0.16 mmol) in 5 cm$^3$ MeOH. After five minutes 253 mg of dppe (0.64 mmol) was added as a solid to the stirred reaction mixture and this was then heated to reflux for one hour. The solution was cooled to room temperature, filtered, and an excess of NH$_4$PF$_6$ (1 g) in 3 cm$^3$ water was added to precipitate an orange compound. This was collected, washed with MeOH (15 cm$^3$) and Et$_2$O (30 cm$^3$), and dried in the air. This gave 95 mg of product (0.08 mmol, 50%). The complex could be recrystallised from CH$_2$Cl$_2$/EtOH. Analysis calculated for C$_{58}$H$_{53}$ClF$_6$N$_2$P$_5$Tc: 58.97% C,4.61% H,2.37% N. Found: 58.92% C,4.68% H,2.70% N.

Method 2

A methanolic solution of [NH$_4$][TcO$_4$] was prepared by adding 0.50 cm of a 0.29 M aqueous solution of [NH$_4$][TcO$_4$] (0.15 mmol) to 3.0 cm$^3$ of reagent grade MeOH. Phenyl hydrazine (50 µl, 0.51 mmol) was then added to this stirred solution. No reaction appeared to take place until 0.1 cm$^3$ of concentrated HCl was added to the reaction mixture five minutes later. This was immediately followed by the addition of 241 mg dppe (0.81 mmol) as a solid. The reaction mixture was heated to reflux for one hour, cooled to room temperature and filtered to remove excess, unreacted dppe. An excess of [NH$_4$][PF$_6$] was added to the stirred solution as a solid and the resultant suspension was stirred at room temperature overnight. The orange precipitate was then collected, washed with $^i$PrOH and Et$_2$O and dried in vacuo to give 108 mg of [Tc(NNPh)(dppe)$_2$Cl][PF$_6$] (0.09 mmol, 60%). The product was identified by comparison of its IR and $^1$H NMR spectra with those obtained from an authentic sample prepared by Method 1.

EXAMPLE 6
The Preparation of [Tc(NNC$_6$H$_4$Cl)(dppe)$_2$Cl][PF$_6$]

This complex was prepared according to Method 2 above from [NH$_4$][TcO$_4$] (0.19 mmol), 129 mg trans-ClC$_6$H$_4$NHNH$_2$.HCl (1.07 mmol), 0.1 cm$^3$ concentrated HCl, and 561 mg dppe (1.41 mmol). Yield of [Tc(NNC$_6$H$_4$Cl) (dppe)$_2$Cl][PF$_6$]: 298 mg, 0.24 mmol, 84%. Analysis calculated for C$_{58}$H$_{52}$Cl$_2$F$_6$N$_2$P$_5$Tc. ½ CH$_2$Cl$_2$: 55.99% C,4.25% H,2.23% N. Found: 55.73% C,4.37% H,1.93% N.

EXAMPLE 7
The reaction of [NBu$_4$][TcOCl$_4$] with Benzoylhydrazine and PPh$_3$ This reaction was performed according to the Method 1 above for the synthesis of Tc(NNPh)$_2$Cl(PPh$_3$)$_2$ using 77 mg [NBu$_4$][TcOCl$_4$], 70 mg PhC[O]NHNH$_2$ (0.51 mmol) and 135 mg PPh$_3$ (0.51 mmol). After the reaction solution had been heated to reflux for one hour and cooled to room temperature, a light orange compound precipitated and was collected, washed with MeOH (15 cm$^3$) and Et$_2$O (30 cm$^3$) and then dried in the air. The compound was identified as TcNCl$_2$(PPh$_3$)$_2$ by comparison of its IR and NMR spectroscopic characteristics with those of an authentic sample.[8] The yield was 97 mg (0.14 mmol, 88%). Analysis calculated for C$_{36}$H$_{30}$Cl$_2$NP$_2$Tc: 61.12% C,4.27% H,1.98% N. Found: 60.66% C,4.35% H,2.32% N.

EXAMPLE 8
The reaction between [NBu$_4$][TcOCl$_4$], Benzoylhydrazine and dppe This reaction was performed according to Method 1 above using 119 mg [NBu$_4$][TcOCl$_4$]0.24 mmol), 91 mg PhC[O]NHNH$_2$ (0.67 mmol), and 323 mg dppe (0.81 mmol). The cooled reaction solution was filtered and an excess of [NH$_4$][PF$_6$] was added with stirring. THe orange complex was identified as [TcN(dppe)$_2$Cl][PF$_6$] by comparison of its spectroscopic properties with those of an authentic sample.[21] Yield: 196 mg (0.18 mmol, 75%). Analysis calculated for C$_{52}$H$_{48}$ClF$_6$NP$_5$Tc: 57.28% C,4.44% H,1.28% N. Found: 56.72% C,4.84% H,0.87% N.

EXAMPLE 9
The reaction between [NBu$_4$][TcOCl$_4$], H$_2$NNH$_2$ and dppe

This reaction was performed by Method 1 above using 124 mg [NBu$_4$][TcOCl$_4$] (0.25 mmol), 15 µl H$_2$NNH$_2$ (Aldrich, Anhydrous, 0.47 mmol) and 421 mg dppe (1.06 mmol). The reaction solution was heated to reflux for 30 minutes, cooled to room temperature, filtered and an excess of [NH$_4$][PF$_6$] was added to the filtrate with stirring. The resultant orange-brown compound was collected by filtration. Yield: 144 mg (0.20 mmol, 80%). This product was identified as the complex [TcN(dppe)$_2$Cl][PF$_6$].

EXAMPLE 10
The Synthesis of TcNNPhMe(PPh$_3$)$_2$Cl$_3$ 108 mg [NBu$_4$][TcOCl$_4$] (0.22 mmol) was dissolved in 10 cm dry MeOH and 52 µl MePhNNH$_2$ (0.44 mmol) was added to the stirred solution. The solution chanced from pale green to red-orange immediately. 211 mg PPh$_3$ (0.80 mmol) was added to the reaction solution and the resulting suspension was heated to reflux for one hour. The resulting suspension was cooled to room temperature and a large amount of a tan precipitate was collected, washed with MeOH (15 cm$^3$) and Et$_2$O (30 cm$^3$ ) and then dried an vacuo. The yield was 108 mg of a complex identified as [Tc(NNPhMe)Cl$_3$(PPh$_3$)$_2$] (0.13 mmol, 59%) Analysis calculated for C$_{43}$H$_{38}$ Cl$_3$N$_2$P$_2$Tc: 60.82% C,4.51% H,3.30% N,12.53% Cl. Found: 60.01% C,4.17% H,3.53% N,12.20% Cl.

EXAMPLE 11
The Preparation of [Tc(NNPhMe)Cl$_2$(PMe$_2$Ph)$_3$][PF$_6$]

A red-orange solution was prepared by adding 0.10 cm$^3$ MePhNNH$_2$ (0.85 mmol) to a stirred solution of 1.47 mg [NBu$_4$][TcOCl$_4$](0.30 mmol) in 4.0 cm$^3$ of MeOH. 0.20 cm$^3$ of PMe$_2$Ph was then added to the reaction mixture and this was then heated to reflux for 45 minutes to give a clear orange solution. The solution was then concentrated to approximately 2 cm$^3$ and then 94 mg [NH$_4$][PF$_6$] was added as a solid to the stirred reaction mixture. The precipitate which formed was collected and washed with 7:1 (v/v) Et$_2$O—$^i$PrOH. The filtrate was reconcentrated to give a second crop of gold-brown microcrystalline material. The yield was 138 mg of [Tc(NNMePh)Cl$_2$(PMe$_2$Ph)$_3$][PF$_6$] (0.16 mmol, 54%). Analysis caluclated for C$_{31}$H$_{40}$C$_2$F$_6$N$_2$P$_4$Tc: 43.93% C,4.76% H,3.31% N. Found: 44.53% C,5.22% H,3.10% N.

EXAMPLE 12
The Preparation of [Tc$^V$(NNPhMe)Cl(Et$_2$NCS$_2$)$_2$]

A red-orange solution was prepared as described above from 138 mg [NBu$_4$][TcOCl$_4$] (0.28 mmol) and 80 µl MePhNNH$_2$ (0.68 mmol) in 3 cm$^3$ of MeOH. After this solution had been stirred at room temperature for five minutes, a solution of 200 mg NaS$_2$CNEt$_2$.3H$_2$O (0.89 mmol) in 2 cm$^3$ MeOH. The resulting dark red solution was heated to reflux for 30 minutes, cooled to room temperature and the solvent was removed in vacuo to give a red, oily residue. This residue was taken up in 5 cm$^3$ of $^i$PrOH and this suspension was filtered to give 73 mg of a pale brown powder which was washed with $Et_2O$. The filtrate was concentrated to about 1–2 cm$^3$ volume and 50 cm$^3$ $Et_2O$ was added. The precipitated thus formed was collected and identical to the original material isolated. The overall yield of the complex, identified as [Tc(NNMePh)Cl(Et$_2$NCS$_2$)$_2$] was 111 mg (0.02 mmol, 71%). The complex could be recrystallised from CH$_2$C$_2$/Et$_2$O. Analysis calculated for $C_{17}H_{27}ClN_4S_4Tc$: 37.12% C,4.95% H,10.19% N,6.44% Cl. Found: 38% C,5% H,11% N,9.4% Cl.

EXAMPLE 13

The Reaction between [NBu$_4$][TcOCl$_4$], MePhNNH$_2$ and dppe

An orange solution was prepared as described above from 100 mg [NBu$_4$][TcOCl$_4$] (0.20 mmol), 45 µl MePhNNH$_2$ (0.38 mmol) in 4 cm$^3$ MeOH. 550 mg dppe (1.38 mmol) was then added to this stirred solution as a solid and the resultant suspension was heated to reflux for one hour, cooled to room temperature and filtered to remove unreacted dppe. An excess of [NH$_4$][PF$_6$] was added as a solid to the filtered solution to give a tan precipitate which was washed with MeOH (20 cm$^3$) and Et$_2$O (10 cm$^3$). This yielded 121 mg of [Tc(NH)O(dppe)$_2$][PF$_6$] (0.11 mmol, 55%). Analysis calculated for $C_{52}H_{49}F_6NOP_5Tc$: 58.27% C,4.61% H,1.31% N. Found: 56.90% C,4.70% H,1.61% N.

EXAMPLE 14

The Reaction of [NBu$_4$][TcOCl$_4$], Me$_2$NNH$_2$ and dppe
Method 1

An orange-red solution was prepared as described above from 211 mg [NBu$_4$][TcOCl$_4$] (0.42 mmol), 35 µl Me$_2$NNH$_2$ (0.46 mmol) in 5 cm$^3$ MeOH and then 366 mg dppe (1.40 mmol) was added as a solid. The reaction mixture was heated to reflux for one hour, cooled to room temperature and a yellow precipitate was collected (72 mg of [Tc(N$_2$)(dppe)$_2$Cl] (0.07 mmol, 17%). An excess of [NH$_4$][PF$_6$] was added as a solid to the filtrate to give a gold-brown precipitate (137 mg) of [Tc(NNMe$_2$)Cl(dppe)$_2$][PF$_6$] (0.12 mmol, 29%).
For [Tc(N$_2$)(dppe)$_2$Cl]
Analysis calculated for $C_{52}H_{48}ClN_2P_4Tc$: 65.17% C,5.05% H,2.92% N. Found: 64.70% C,5.32% H,2.07% N.
For [Tc(NNMe$_2$)Cl(dppe)$_2$][PF$_6$]
Analysis calculated for $C_{54}H_{52}ClF_6P_5Tc$: 57.33% C,4.63%. H,2.48% N. Found: 51.6% C,4.4% H,1.8% N.
Method 2

A reaction solution was prepared as for Method 1 from 95 mg [NBu$_4$][TcCl$_4$]0.19 mmol), 27 µl Me$_2$NNH$_2$ (0.36 mmol), 333 mg dppe (0.84 mmol) in 5 cm MeOH. This reaction mixture was stirred at room temperature for 70 hours. The reaction solution was filtered to remove excess dppe (no yellow precipitate was observed), 65 mg NH$_4$PF$_6$ (0.40 mmol) was added to the filtrate as a solid and the solution was then concentrated in vacuo and the residue was taken up in 5 cm$^3$ CH$_2$Cl$_2$. This solution was filtered to remove undissolved inorganic salts. After filtration, 25 cm$^3$ iPrOH was added to the filtrate to give 135 mg of a yellow-brown solid which was collected, washed and dried. This was identified by comparison of the IR spectrum of this complex with that of [Tc(NNMe$_2$)Cl(dppe)$_2$][PF$_6$] prepared by Method 1 (0.12 mmol, 63%).

EXAMPLE 15

The Reaction of [NBu$_4$][TcOBr$_4$], Me$_2$NNH$_2$ and dppe

This was performed by Method 1 for the reaction described above for [NBu$_4$][TcOCl$_4$] using 130 mg [NBu$_4$][TcOBr$_4$]0.20 mmol), 20 µl Me$_2$NNH$_2$ (0.26 mmol), 247 mg dppe (0.62 mmol) in 5 cm MeOH. This gave 55 mg of a yellow complex, Tc(N$_2$)Br(dppe)$_2$ (0.06 mmol, 30%). No salts were isolated from the reaction filtrate after the addition of an excess of NH$_4$PF$_6$ to the solution. Analysis calculated for $C_{52}H_{48}BrN_2P_4Tc$: 62.22% C,4.82% H,2.79% N. Found: 58.48% C,4.71% H,2.03% N.

$^{99m}$Tc Complexes

General: The $^{99m}$Tc diazenide and hydrazide (2–) complexes were prepared in a straightforward fashion from the appropriate hydrazine, $^{99m}$TcO$_4^-$ and a suitable ligand. The complex preparations were found to yield the desired cationic products in reasonably high radiochemical purity (see Tables 2–4). The main contaminants in these preparations were the [Tc$^{III}$Cl$_2$(L)$_2$]$^+$ cations, as verified by comparison of HPLC and TLC characteristics of these impurities with authentic samples of these Tc$^{III}$ species prepared by a literature method.[22] There is some question in the case of the MePhNNH$_2$ labelled species whether the complexes formed are of the formulation [Tc$^{IV}$ (NNMePh)Cl(L)$_2$]$^+$ or [Tc$^V$ (NH)O(L)$_2$]+. Recent ICES studies on the preparation obtained from the labelling where L=P65 (mmmpe) have shown that the oxidation state of the complex obtained is +4.[23] This indicates that the species present in the MePhNNH$_2$ preparations are the desired hydrazido (2–) species.

Reagents: The ligands used are given in Table 1. All other reagents used were from commercial suppliers and used as received. [$^{99m}$TcO$_4$]$^-$ was obtained as solutions in physiological saline from Amertec II generators. Reaction products were analyzed by HPLC, TLC and gel electrophoresis as described elsewhere.[24] All preparations were performed under an atmosphere of nitrogen gas.

EXAMPLE 16

Complex Preparation: 20–25 µl of hydrazine was added to 2 cm$^3$ of absolute ethanol, then $^{99m}$TcO$_4^-$(0.2–3.0 GBq) and 10 mg of ligand were added to the solution. This mixture was heated to 120° C. for 30–60 minutes, cooled to room temperature and analyzed.

For biodistribution studies the total volume of the preparation was made up to 5 cm$^3$ by the addition of sterile saline solution.

Animal Biodistribution Studies: Six male Sprague Dawley rats were injected while under light ether anaesthesia with 0.1 cm$^3$ of preparation (i.v., tail vein) and half were sacrificed by cervical dislocation while under ether anaesthesia at the appropriate time interval post-injection and dissected. Organs were weighed and their activities measured in an ionisation chamber. For the purposes of calculations blood was assumed to constitute 5.8% of the total body weight, muscle was assumed to be 43% and the lungs were assumed to weigh 1 g.

Biodistribution results are given in Tables 2–4.

TABLE 1

Ligands used in $^{99m}$Tc labelling work

| Abbreviation | Structure | Name |
|---|---|---|
| dmpe | 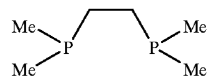 | 1,2-bis(dimethylphosphino)ethane |
| dppe | 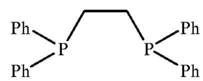 | 1,2-bis(diphenylphosphino)ethane |
| P56 | 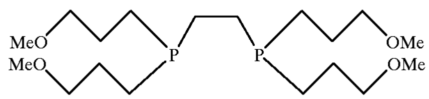 | 1,2-bis(di(3-methoxypropyl)phosphino)ethane |
| PL28 | 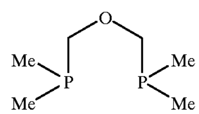 | bis((dimethylphosphino)methyl)ether |
| P46 | 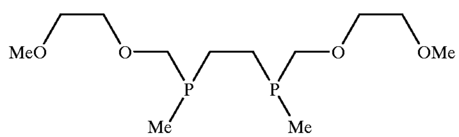 | 1,2-bis((2'-methoxy)ethoxymethyl)methylphosphino)ethane |
| PL34 | 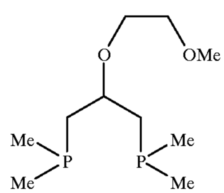 | 1,3-bis(dimethylphosphino)-2-((2-methoxy)ethoxy)propane |
| PL38 | 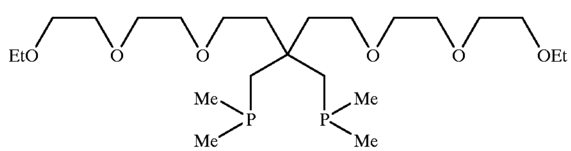 | 1-3-bis(dimethylphosphino)-2,2-bis(2-(2-ethoxy)ethoxy)ethoxymethyl)propane; or 1,3-bis(dimethylphosphino)-2,2-(2,5,8-trioxadecyl)propane |
| PL31 | 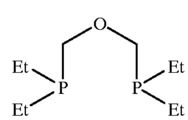 | bis((diethylphosphino)methyl)ether |
| P53 | 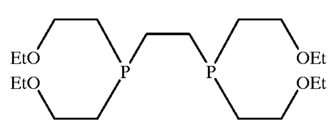 | 1,2-bis(di(2'-ethoxy)ethyl)phosphino ethane |
| P65 | 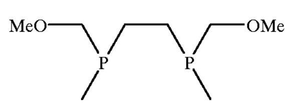 | 1,2-bis((methoxymethyl)methyl phosphine)ethane |

TABLE 1-continued

Ligands used in $^{99m}$Tc labelling work

| Abbreviation | Structure | Name |
|---|---|---|
| PL37 | 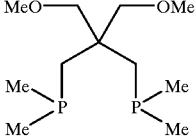 | 1,3-bis(dimethylphosphine)-2,2-bis(methoxymethyl)propane |
| PL40 | 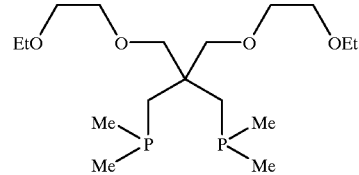 | 1,3-bis(dimethylphosphino)-2,2-bis(2',5'-dioxaheptyl)propane |
| PL42 | 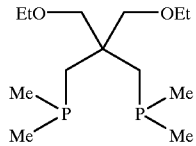 | 1,3-bis(dimethylphosphino)-2,2-bis(ethoxymethyl)propane |
| PL43 | 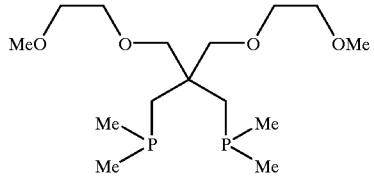 | 1,3-bis(dimethylphosphino)-2,2-bis((2'-methoxy)ethoxymethyl)propane |
| PL46 | 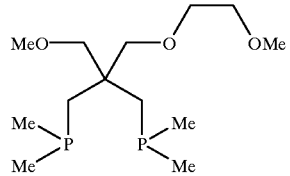 | 1,3-bis(dimethylphosphino)-2-(methoxymethyl)-2-((2'methoxy)ethoxymethyl)propane |
| PL49 | 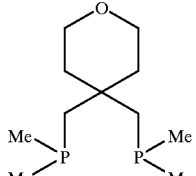 | 4,4-bis((dimethylphosphino)methyl)tetrahydropyran |
| PL50 | 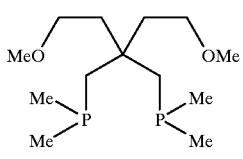 | 1,3-bis(dimethylphosphino)-2,2-bis(methoxyethyl)propane |
| P68 | 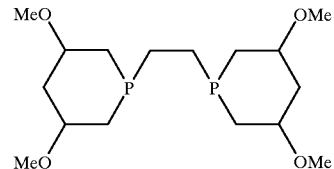 | 1,2-bis(di((2'methoxy)propyl)phosphino)ethane |

TABLE 2

Biodistributions of Phenyldiazenide $^{99m}$Tc species in Rats

| Notebook | IV23 | | VI12 | | VI9 | |
|---|---|---|---|---|---|---|
| Ligand | dmpe | | PL28 | | P46 | |
| MEK | 60 | | 84 | | 80 | |
| RCP (%) HPLC | 40 | | 70 | | 75 | |
| Time P.I. | 2 | 60 | 2 | 60 | 2 | 60 |
| Heart | 0.91 (14) | 0.78 (03) | 1.12 (11) | 0.65 (06) | 0.96 (04) | 0.80 (02) |
| Blood | 6.98 (71) | 1.10 (02) | 4.18 (05) | 0.46 (04) | 7.45 (63) | 1.01 (16) |
| Muscle | 22.8 (3.0) | 14.0 (3.7) | 30.2 (3.0) | 27.4 (3.6) | 21.4 (3.1) | 17.0 (4.0) |
| Lung | 1.88 (14) | 0.86 (10) | 1.18 (14) | 0.62 (05) | 1.41 (27) | 0.36 (05) |
| Liver | 22.2 (2.6) | 10.5 (8) | 17.8 (2.9) | 5.95 (57) | 26.0 (1.0) | 6.92 (1.23) |
| S.I. | 13.2 (8) | 36.7 (4) | 13.2 (1.0) | 39.6 (2.7) | 11.0 (3.2) | 44.0 (1.9) |
| Kidney | 11.2 (8) | 9.91 (1.25) | 9.41 (0.30) | 5.90 (06) | 9.62 (48) | 2.88 (16) |
| Bladder & Urine | 0.11 (03) | 11.3 (4) | 0.11 (06) | 10.9 (5.9) | 0.11 (05) | 17.8 (2.6) |
| Brain | 0.06 (01) | 0.02 (01) | 0.04 (00) | 0.02 (00) | 0.05 (01) | 0.01 (00) |
| H/Bl | 1.97 (05) | 9.52 (33) | 3.97 (32) | 21.3 (0.8) | 2.05 (29) | 13.2 (2.1) |
| H/Li | 0.54 (11) | 0.93 (11) | 0.82 (19) | 1.56 (12) | 0.58 (06) | 1.79 (30) |

| Notebook | VI31 | | LH2.17 | | LH2.30 | |
|---|---|---|---|---|---|---|
| Ligand | P46 (HPLC purified) | | PL42 | | PL43 | |
| MEK | 50 | | 65 | | 26 | |
| RCP (%) HPLC | 50 | | 70 | | 50 | |
| Time P.I. | 2 | 60 | 2 | 60 | 2 | 60 |
| Heart | 1.05 (09) | 0.96 (04) | 1.22 (30) | 1.19 (20) | 0.55 (03) | 0.26 (03) |
| Blood | 7.00 (0.31) | 0.78 (08) | 28.6 (1.4) | 8.99 (2.28) | 21.5 (3.5) | 1.14 (36) |
| Muscle | 21.0 (3.1) | 21.3 (2.3) | 18.1 (0.5) | 21.3 (0.3) | 21.7 (2.4) | 10.9 (1.3) |
| Lung | 1.33 (14) | 0.47 (05) | 2.56 (33) | 1.57 (32) | 1.47 (04) | 0.22 (03) |
| Liver | 22.1 (2.0) | 4.94 (77) | 22.8 (3.2) | 14.7 (1.6) | 21.4 (1.6) | 9.08 (2.03) |
| S.I. | 11.5 (3.2) | 39.8 (0.3) | 7.66 (18) | 31.8 (2.0) | 8.6 (0.5) | 45.6 (6.8) |
| Kidney | 11.1 (2.1) | 3.31 (17) | 5.35 (46) | 3.52 (47) | 9.19 (74) | 2.32 (32) |
| Bladder & Urine | 1.01 (1.49) | 17.0 (4.3) | 0.06 (01) | 2.61 (23) | 0.16 (06) | 25.4 (4.6) |
| Brain | 0.04 (00) | 0.01 (00) | — | — | — | — |
| H/Bl | 2.37 (12) | 18.9 (1.6) | 0.59 (12) | 2.13 (43) | 0.41 (06) | 3.83 (1.03) |
| H/Li | 0.66 (12) | 2.77 (36) | 0.73 (24) | 1.12 (26) | 0.38 (03) | 0.40 (03) |

| Notebook | LH2.51 | | PAH1.26 | | VI28 | |
|---|---|---|---|---|---|---|
| Ligand | P65 | | PL50 | | PL38 | |
| MEK | 60 | | 70 | | 86 | |
| RCP (%) HPLC | 85 | | 75 | | 80 | |
| Time P.I. | 2 | 60 | 2 | 60 | 2 | 60 |
| Heart | 1.20 (11) | 1.08 (09) | 0.83 (09) | 0.65 (04) | 1.04 (06) | 0.65 (09) |
| Blood | 5.73 (58) | 1.05 (09) | 4.38 (25) | 0.42 (03) | 4.51 (1.36) | 0.16 (02) |
| Muscle | 27.8 (8.4) | 23.6 (7.7) | 18.7 (2.5) | 14.9 (2.7) | 21.0 (5.1) | 16.2 (4.1) |
| Lung | 1.61 (18) | 0.53 (08) | 1.02 (12) | 0.43 (06) | 1.41 (13) | 0.35 (11) |
| Liver | 22.0 (1.8) | 6.68 (1.19) | 34.8 (1.2) | 4.35 (30) | 28.4 (1.6) | 9.27 (35) |
| S.I. | 11.2 (2.1) | 39.8 (4.3) | 12.8 (0.7) | 57.9 (2.4) | 11.5 (2.0) | 57.0 (2.8) |
| Kidney | 12.0 (1.2) | 3.71 (07) | 12.0 (0.30) | 6.81 (56) | 10.7 (1.9) | 4.01 (44) |
| Bladder & Urine | 0.11 (0.05) | 9.95 (66) | 0.09 (03) | 6.76 (65) | 0.14 (04) | 5.81 (1.46) |
| Brain | — | — | — | — | 0.13 (00) | 0.00 (00) |
| H/Bl | 3.33 (30) | 15.8 (1.0) | 2.68 (22) | 22.2 (0.4) | 3.59 (88) | 62.5 (7.0) |
| H/Li | 0.81 (12) | 2.33 (32) | 0.31 (04) | 1.27 (96) | 0.48 (01) | 1.05 (17) |

TABLE 3

Biodistributions of [Tc$^{III}$(NNC$_6$H$_4$NO$_2$) (Cl(dmpe)$_2$]$^+$ in Rats

| Notebook | CMAIV78 | |
|---|---|---|
| Ligand | dmpe | |
| MEK | 86 | |
| RCP (%) HPLC | 65 | |
| Time P.I. | 2 | 60 |
| Heart | 1.15 (22) | 0.67 (05) |
| Blood | 5.68 (66) | 0.92 (07) |
| Muscle | 26.2 (7.7) | 16.8 (1.2) |
| Lung | 2.27 (15) | 1.04 (23) |
| Liver | 22.4 (3.9) | 12.3 (0.7) |
| S.I. | 13.0 (3.1) | 33.8 (3.2) |
| Kidney | 9.47 (25) | 9.47 (33) |
| Bladder & Urine | 0.08 (02) | 7.28 (1.10) |
| Brain | 0.12 (00) | 0.06 (00) |

TABLE 3-continued

Biodistributions of [Tc$^{III}$(NNC$_6$H$_4$NO$_2$) (Cl(dmpe)$_2$]$^+$ in Rats

| Notebook | CMAIV78 | |
|---|---|---|
| Ligand | dmpe | |
| MEK | 86 | |
| RCP (%) | 65 | |
| HPLC | | |
| Time P.I. | 2 | 60 |
| H/Bl | 3.00 (49) | 11.0 (0.9) |
| H/Li | 0.72 (28) | 0.76 (12) |

TABLE 4

Biodistributions of $^{99m}$Tc-hydrazide (2-) species in Rats and Guinea Pigs

| Notebook | PAH2.14 | | CMAIV58 | | CMAVI41 | |
|---|---|---|---|---|---|---|
| Ligand | P65 | | dmpe | | dmpe (HPLC purified) | |
| MEK | 86 | | 78 | | 83 | |
| RCP (%) HPLC | 90 | | 70 | | 73 | |
| Time P.I. | 2 | 60 | 2 | 60 | 2 | 60 |
| Heart | 0.95 (09) | 0.69 (03) | 1.13 (13) | 0.80 (08) | 1.25 (08) | 0.99 (15) |
| Blood | 4.77 (10) | 0.69 (13) | 7.84 (47) | 1.05 (11) | 7.95 (21) | 1.05 (21) |
| Muscle | 26.1 (5.8) | 20.2 (2.7) | 27.9 (4.9) | 20.6 (3.2) | 26.3 (5.2) | 19.3 (4.9) |
| Lung | 1.58 (0.36) | 0.33 (02) | 2.36 (37) | 1.14 (07) | 2.40 (0.21) | 1.28 (20) |
| Liver | 22.8 (1.4) | 9.23 (26) | 22.2 (0.6) | 11.6 (1.6) | 21.1 (1.7) | 10.8 (1.9) |
| S.I. | | | 10.5 (2.2) | 30.6 (3.4) | 11.9 (3.2) | 31.1 (4.5) |
| Kidney | 7.76 (12) | 1.95 (15) | 9.95 (1.40) | 11.1 (0.4) | 10.8 (0.6) | 11.6 (1.3) |
| Bladder & Urine | | | 0.08 (01) | 6.84 (77) | 0.12 (07) | 4.70 (93) |
| Brain | | | 0.05 (01) | 0.03 (01) | 0.07 (01) | 0.04 (01) |
| H/Bl | 3.25 (27) | 15.0 (3.4) | 2.43 (12) | 12.2 (1.4) | 2.27 (21) | 14.2 (2.4) |
| H/Li | 0.64 (06) | 1.11 (02) | 0.78 (13) | 1.06 (13) | 0.82 (04) | 1.30 (41) |

| Notebook | CMAVI15 | | CMAVI36 | | CMAVI36 |
|---|---|---|---|---|---|
| Ligand | P46 | | P46* (HPLC purified) | | P46 (HPLC purified) |
| | | | | | RATS |
| MEK | 64 | | 54 | | 54 |
| RCP (%) HPLC | 65 | | 53 | | 53 |
| Time P.I. | 2 | 60 | 2 | 60 | 60 |
| Heart | 0.81 (07) | 0.58 (04) | 0.96 (12) | 0.65 (03) | 0.97 (06) |
| Blood | 7.10 (0.51) | 0.50 (05) | 10.1 (1.7) | 0.89 (12) | 0.27 (02) |
| Muscle | 28.4 (2.5) | 18.4 (2.5) | 21.9 (3.3) | 28.5 (2.2) | 20.0 (1.2) |
| Lung | 1.33 (09) | 0.30 (07) | 1.30 (05) | 0.51 (11) | 0.36 (10) |
| Liver | 23.3 (0.5) | 7.23 (70) | 15.9 (1.1) | 5.18 (36) | 8.29 (67) |
| S.I. | 9.38 (3.20) | 44.8 (2.6) | 11.3 (1.2) | 15.0 (7.1) | 43.6 (2.2) |
| Kidney | 9.37 (52) | 2.13 (10) | 13.0 (1.6) | 11.0 (0.3) | 4.05 (66) |
| Bladder & Urine | 0.18 (10) | 19.2 (1.6) | 0.22 (17) | 10.6 (1.1) | 12.7 (1.0) |
| Brain | 0.04 (02) | 0.51 (13) | — | — | — |
| H/Bl | 1.65 (08) | 16.5 (1.0) | 2.89 (53) | 17.8 (2.1) | 58.7 (7.0) |
| H/Li | 0.48 (03) | 1.01 (13) | 0.88 (10) | 1.89 (0.22) | 1.68 (14) |

*In Guinea Pigs

EXAMPLES 17–19

All reactions were performed under an atmosphere of dinitrogen using predried, distilled solvents unless noted otherwise. [Bu$_4$N][TcOCl$_4$] was prepared by the literature procedure.[28]

EXAMPLE 17
Technetium Diazenido-Starting Materials
a) [TcCl(NNC$_6$H$_4$Cl)$_2$(PPh$_3$)$_2$] 9
Method 1. From [Bu$_4$N][TcOCl$_4$]

[Bu$_4$N][TcOCl$_4$] (0.134 g, 0.268 mmol), 4-ClC$_6$H$_4$NHNH$_2$.HCl (0.120 g, 0.67 mmol, 2.5 equivalents), Et$_3$N (0.09 ml, 0.67 mmol), and PPh$_3$ (0.211 g, 0.804 mmol, 3 equivalents) in dry methanol (5 ml) were stirred for 2 hours at room temperature. The khaki solid was collected by filtration, washed with methanol and ether and dried. (yield 0.134 g, 53%). The product could be recrystallised from CH$_2$Cl$_2$/MeOH yielding bright orange crystals. (Found: C,61.23; H,3.98; N,6.05; Cl,11.74. TcC$_{48}$H$_{38}$N$_4$P$_2$Cl$_3$ requires C,61.45; H,4.08; N,5.97; Cl,11.34). HPLC retention time 9.4 minutes, single species. $v_{max.}$ (KBr plates, nujol mull) 1600, 1555 cm$^{-1}$ (NN). $^{31}$P NMR (CDCl$_3$) 30.27 ppm singlet.

Method 2. From [NH$_4$][TcO$_4$]

Aqueous [NH$_4$][TcO$_4$] (0.5 ml, 0.181 mmol) was evaporated to dryness in vacuo. ClC$_6$H$_4$NHNH$_2$. HCl (0.142 g, 0.793 mmol) in dry methanol (2.5 ml) was added with stirring to give an orange solution after 10 minutes. Solid PPh$_3$ (0.204 g, 0.778 mmol) was added and the mixture heated under reflux for 1.5 hours. After cooling to room temperature the khaki solid was collected by filtration and washed with ether (yield 0.113 g, 67%). The product could be crystallised from CH$_2$Cl$_2$/MeOH to yield an orange crystalline solid which has an identical IR spectrum to an authentic sample of 9 prepared from t[TcOCl$_4$]$^-$.

b) [TC(NNC$_6$H$_4$CH$_3$)$_2$(PPh$_3$)$_2$] 10

[Bu$_4$N][TcOCl$_4$] (0.178 g, 0.356 mmol), CH$_3$C$_6$H$_4$NHNH$_2$.HCl (0.282 g, 1.78 mmol, 5 equivalents), Et$_3$N (0.25 ml, 1.78 mmol), and PPh$_3$ (0.280 g, 1.07 mmol, 3 equivalents) were stirred in dry methanol (5 ml) overnight to give a khaki suspension. The product was collected by filtration, washed with ether and dried (yield 0.122 g, 40%). HPLC retention time 10.4 minutes, one major species. Analysis on the crude material gave (Found: C,64.1; H,4.6; N,5.9; Cl,3.53. TcC$_{50}$H$_{44}$N$_4$P$_2$Cl requires C,66.93; H,4.94;

N,6.24; Cl,3.95%). $^1$H NMR (CDCl$_3$) 2.29[6H, s, 2×CH$_3$], 6.5–8.0 [38H, m, phenyl H]. $^{31}$P NMR (CDCl$_3$) 28.6 ppm singlet. $v_{max.}$ 1620, 1570, 1535 cm$^{-1}$ (NN). The product may be recrystallised from CH$_2$Cl$_2$/MeOH.

c) [TcCl$_2$(NNC$_6$H$_4$NO$_2$)(PPh$_3$)$_2$] 11

[Bu$_4$N][TcOCl$_4$](0.152 g, 0.304 mmol), O$_2$NC$_6$H$_4$NHNH$_2$ (0.116 g, 0.76 mmol, 2.5 equivalents), and PPh$_3$ (0.239 g, 0.912 mmol, 3 equivalents) in dry methanol (5 ml) were stirred overnight to give a pale orange solid which was collected by filtration (yield 0.223 g, 77%). This was recrystallised from CH$_2$Cl$_2$/MeOH to give a lime-green solid (0.151 g, 52%). $v_{max.}$ 1620, 1600 (NN), 1555 (NO$_2$), 1335 (NO$_2$) cm$^{-1}$. $^1$H NMR (CDCl$_3$) 3.4 [MeOH], 7.0–8.0 [phenyl H]. $^{31}$P NMR (CDCl$_3$) 30.0 ppm singlet. HPLC retention time 10.4 minutes. (Found: C,57.65; H,4.18; N,4.94; Cl,8.60. Found: C,57.42; H,4.24; N,4.95; Cl,7.95. TcC$_{43}$H$_{38}$N$_3$Cl$_2$O$_3$P$_2$ requires C,58.92; H,4.37; N,4.79; Cl,8.09%).

EXAMPLE 18
Substitution Chemistry of the Technetium Diazenido-Starting Materials a) [TcCl(NNC$_6$H$_4$Cl)(dppe)$_2$][BPh$_4$] 12

9 (0.098 g, 0.104 mmol) and dppe (0.104 g, 0.26 mmol, 2.5 equivalents) in methanol-toluene (1:1, 4 ml) were heated under reflux for 3 hours to give a dark orange solution. Solid NaBPh$_4$ (0.035 g, 1 equivalent) was added with stirring to precipitate an orange solid. The product was collected by filtration (yield 0.117 g, 77%). The crude product could be recrystallised from CH$_2$Cl$_2$/ether. (Found: C,70.55; H,5.34; N,2.17; Cl,4.72. TcC$_{80}$H$_{72}$N$_2$B$_{42}$ requires C,70.34; H,5.31; N,2.05; Cl,5.19%). HPLC retention time 14 minutes. $v_{max.}$ 1575, 1665 cm$^{1-}$ (NN). $^1$H NMR (CDCl$_3$) 2.68[8H, broad m, 2x —CH$_2$CH$_2$—], 6.5–7.5[64H, broad unresolved m, phenyl H].

b) [TcCl(NNC$_6$H$_4$Cl)(dppe)$_2$][PF$_6$] 12a

This was prepared in an analogous fashion to 12 using 9 (0.101 g, 0.107 mmol) and dppe (0.107 g, 0.269 mmol) in methanol/toluene (1:1, 4 ml) under reflux for 1 hour. [NH$_4$][PF$_6$] (0.018 g, 0.110 mmol) was added with stirring to the filtered reaction mixture to give 12a (yield 0.059 g, 43%). This could be recrystallised from CH$_2$Cl$_2$/MeOH (Found: C,55.44; H,4.27; N,2.48; Cl,6.35. TcC$_{58}$H$_{44}$N$_2$P$_5$Cl$_2$ F$_6$ requires C,57.68; H,3.67; N,2.32; Cl,5.87%).

c) [TcCl(NNC$_6$H$_4$NO$_2$)(dppe)$_2$][BPh$_4$] 13

11 (0.051 g, 0.06 mmol) and dppe (0.060 g, 0.151 mmol, 2.5 equivalents) in methanol/toluene (1:1, 3 ml) were heated under reflux for 1 hour to give an orange-red solution. After cooling to room temperature solid NaBPh$_4$(0.02 g, 1 equivalent) was added with stirring to precipitate the product as an orange solid. This was collected by filtration and washed with MeOH and Et$_2$O (yield 0.06 g, 72%). The product was recrystallised from CH$_2$Cl$_2$/Et$_2$O (yield 0.042 g, 50%) as an orange crystalline solid. $v_{max.}$ 1645s, 1600w (NN), 1570 (NO$_2$), 1340 (NO$_2$) cm$^{-1}$. HPLC retention time 14.2 minutes, single peak. (Found: C,67.65; H,5.12; N,2.93; Cl,4.14. TcC$_{82}$H$_{72}$N$_3$O$_2$Cl—P$_4$B.½CH$_2$Cl$_2$ requires C,68.66; H,5.10; N,2.91; Cl,4.91%).

d) [Tc(NNC$_6$H$_4$Cl)(S$_2$CNMe$_2$)$_2$(PPh$_3$)] 14

9 (0.139 g, 0.148 mmol) and NaS$_2$CNMe$_2$ (0.08 g, 0.444 mmol, 3 equivalents) in absolute ethanol (2 ml) were heated under reflux for 1.5 hours. The orange solid was collected by filtration after cooling (yield 0.072 g) and redissolved in CH$_2$Cl$_2$ before passage down a Fluorsil column eluting the orange band with CH$_2$Cl$_2$. This eluate was evaporated to dryness and the residue recrystallised from CH$_2$Cl$_2$/Et$_2$O to give dark orange crystals (yield 0.072 g, 66%). HPLC retention time 13.6 minutes, single species. (Found: C,45.82; H,4.09; N,6.79; Cl,6.25. Found: C,45.99; H,4.04; N,6.77. TcC$_{30}$H$_{31}$N$_4$ClS$_4$P.½CH$_2$Cl$_2$requires C,46.74; H,4.11, N,7.15; Cl,9.05. TcC$_{30}$H$_{31}$N$_4$ClS$_4$P.¼CH$_2$Cl$_2$ requires C,47.65; H,4.16, N,7.35; Cl,6.97%). $^1$H NMR (CDCl$_3$) 2.92[3H, s, CH$_3$], 3.06[3H, s, CH$_3$], 3.31[3H, s, CH$_3$], 3.39[3H, s, CH$_3$], 5.27[CH$_2$Cl$_2$], 6.8–7.7[19H, m, phenyl H]. $^{31}$P NMR (CDCl$_3$) no signal was observed in this sample at room temperature.

e) [TcCl(NNC$_6$H$_4$Cl)(maltol)(PPh$_3$)$_2$] 15

9(0.145 g, 0.155 mmol) and maltol (0.059 g, 0.465 mmol, 3 equivalents) in absolute ethanol (2 ml) were heated under reflux for 2 hours. After cooling to room temperature the orange product was collected by filtration and washed with ethanol. The product was recrystallised from CH$_2$Cl$_2$/ether (yield 0.03 g, 21%) as dark orange crystals. (Found: C,59.68; H,4.11; N,3.03; Cl,7.73. TcC$_{48}$H$_{39}$N$_2$Cl$_2$O$_3$P$_2$ requires C,62.41; H,4.23; N,3.03, Cl,7.68%). $v_{max.}$ 1615s, 1560 cm$^{-1}$. $^1$H NMR (CDCl$_3$) 2.21[3H, s, CH$_3$], 5.63(1H, d, J$_{HH}^3$=4 Hz, C=CH], 6.92[1H, d, J$_{HH}^3$=4 Hz, C=CH], 7.0–8.0[34H, m phenyl H]. $^{31}$P NMR (CDCl$_3$) 30.0 ppm singlet. HPLC retention time 10 minutes.

f) [Tc(NNC$_6$H$_4$Cl)(salen)(PPh$_3$)] 16

9 (0.100 g, 0.107 mmol), salenH$_2$ (0.032 g, 0.119 mmol, 1.1 equivalents), and Et$_3$N (0.40 ml, 0.259 mmol, 2.2 equivalents) in dry methanol/toluene (1:1, 3 ml) were heated under reflux for 2 hours. After cooling, addition of ether gave a khaki-green solid which was collected by filtration, washed with ether and dried (yield 0.052 g, 63%). The product could be recrystallised from CH$_2$Cl$_2$/heptane as very dark green crystals. (Found: C,61.77; H,4.41; N,7.17; Cl,4.77. TcC$_{40}$H$_{33}$N$_4$PO$_2$Cl requires C,62.63; H,4.34; N,7.30; Cl,4.62%). $v_{max.}$ 1600, 1610, 1620 (NN), 1540 (C=N) cm$^{-1}$. $^1$H NMR (CDCl$_3$) 4.0[4H, broad m, —CH$_2$CH$_2$—], 6.0–7.6[27H, broad m, phenyl H], 8.14[2H, s, N=CH]. $^{31}$P NMR (CDCl$_3$) no signal was observed at room temperature. HPLC retention time 11.6 minutes.

g) [Tc(NNC$_6$H$_4$Cl)$_2$(N$_2$S$_2$)]$_x$ 17 N$_2$S$_2$=(HSCH(Me)CONHCH$_2$—)$_2$ 9 (0.083 g, 0.088 mmol), N$_2$S$_2$ (0.023 g, 0.097 mmol, 1.1 equivalents), and Et$_3$N (0.05 ml, 0.34 mmol, 4 equivalents) in dry methanol (2 ml) were heated under reflux for 1 hour to give a dark brown-green solution. The solvent was removed in vacuo and the brown oil triturated with isopropanol to give a dark brown solid product (yield 0.011 g). The product was too insoluble for satisfactory recrystallisation and analysis by NMR, but appeared to be diamagnetic. HPLC retention time 12.2 minutes. (Found: C,40.36; H,4.40; N,9.19; Cl,11.97. TcC$_{20}$H$_{24}$N$_4$C$_2$S$_2$O$_2$ requires C,40.96; H,4.12; N,9.55; Cl,12.09%).

EXAMPLE 19
Technetium Imido Complexes
[TcCl (NC$_6$H$_4$CO$_2$)(PPh$_3$)$_2$] 18
Method 1. From [NH$_4$][TcO$_4$]

Aqueous [NH$_4$][TcO$_4$] (1 ml, 0.343 mmol), 2-HO$_2$CC$_6$H$_4$NH$_3$Cl (2-carboxyaniline hydrochloride) (0.298 g, 1.715 mmol, 5 equivalents), and PPh$_3$ (0.360 g, 1.372 mmol, 4 equivalents) in reagent grade methanol (10 ml) were stirred overnight to give a bright green precipitate. The product was collected by filtration, washed with MeOH, ether and dried i vacuo (yield 0.139 g, 50%). (Found: C,63.30; H,4.44; N,1.77. TcC$_{43}$H$_{34}$ NO$_2$P$_2$Cl requires C,62.33; H,4.14; N,1.67%). The product was soluble in DMF and CH$_2$Cl$_2$.

Method 2. From [Bu$_4$N][TcOCl$_4$]

[Bu$_4$N][TcOCl$_4$] (0.262 g, 0.525 mmol), anthranilic acid (0.72 g, 5.25 mmol, 10 equivalents), and PPh$_3$(0.48 g, 1.84 mmol, 3.5 equivalents) in absolute ethanol (20 ml) were heated under reflux for 2 hours. The hot solution was filtered (air) and taken to dryness in vacuo. The residue was then triturated with ether and the solid green product isolated after filtration was recrystallised from EtOH/hexane (yield 0.114 g, 26%). $^{31}$P NMR (DMSO) 31.2 ppm singlet.

REFERENCES

1. E. Deutsch, K. Libson, S. Jurisson, and L. F. Lindoy, *Progr. Inorg. Chem.*, (1983), 30, 75.
2. Clark, M. J.; Podbielski, L. *Coord. Chem. Rev.*, 1987, 78, 253.
3. I. Rothwell in 'Comprehensive Coordination Chemistry', Vol 2 (eds. G. Wilkinson, R. D. Gillard, and J. A. McCleverty) Pergamon Press (1987).
4. D. Bright and J. A. Ibers, *Inorg. Chem.*, (1968), 7, 1099.
5. D. Bright and J. A. Ibers, *Inorg. Chem.*, (1969), 8, 703.
6. G. V. Goeden and B. L. Haymore, *Inorg. Chem.* (1983), 22, 157.
7. D. C. Bradley, M. B. Hursthouse, K. M. A. Malik, A. J. Nielson, and R. L. Short, *J. Chem. Soc., Dalton Trans.*, (1983), 2651.
8. E. A. Maatta, *Inorg. Chem.*, (1984), 23, 2560.
9. C. Y. Chou, J. C. Huffman, and E. A. Maatta, *J. Chem. Soc., Chem. Commun.*, (1984), 1184
10. a. Johnson, B. F. G.; Haymore, B. L.; Dilworth J. R. in "Comprehensive Coord. Chem." , Wilkinson, G.; Gillard, R. D.; McCleverty, J. A., eds.; Pergamon Press: Oxford, 1988.
    b. Nugent, W. A.; Haymore, B. L. *Coord. Chem. Rev.*, 1980, 31, 123–175.
    c. Hsieh, T. -C.; Shaikh, S. N.; Zubieta, J. *Inorg. Chem.*, 1987, 26, 4079.
11. Golton, R.; Tomkins, I. B.; Wilson, P. W. *Aust. J. Chem.*, 1964, 17, 496–7.
12. Dilworth, J. R., Morton, S. *Transition Met. Chem.*, 1987, 12, 41.
13. Moore, F. W.; Larson, M. L. *Inorg. Chem.*, 1967, 6, 988.
14. Chatt, J.; Crichton, B. A. L.; Dilworth, J. R.; Dahlstrom, P.; Gutkoska, R; Zubieta, J. *Inorg. Chem.*, 1982, 21, 2383.
15. Kaden, L.; Lorenz, B.; Schmidt, K.; Sprinz, H.; Wahren, M. *Isotopenpraxis*, 1981, 17, 174.
16. Abram, S.; Abram, U.; Spies, H.; Munze, R.; J. Radioanal. Nucl. Chem., 1986, 102, 309–370.
17. I. S. Kolomnikov, Yu. D. Koreshkov, T. S. Lobeeva, and M. E. Volpin, *J. Chem. Soc., Chem. Commun.*, (1979), 1432.
18. C. M. Archer and J. R. Dilworth, Unpublished Results.
19. F. Refosco, U. Mazzi, E. Deutsch, J. R. Kirchoff, W. R. Heineman, and R. Seeber, *Inorg. Chem.*, (1988), 27, 4121.
20. Davison, A.; Trop, H. S.; De Pamphilis, B. V.; Jones, A. G. Inorg. Synth., 1982, 21, 160.
21. Dilworth, J. R.; Archer, C. M., unpublished results.
22. Neirinckx, R. D.: U.S. Pat. No. 4,419,339, Dec. 6, 1983 (Chem. Abs. 100: P73987v).
23. Burke, J. F.; Archer, C. M.; Chiu, K. W.; Latham, I. A; Edgell, R. G., unpublished results.
24. Chiu, K. W.; Kelly, J. D.; Latham, I. A.; Griffiths, D. V.; Edwards, P. G. European Patent Application No. 0311352 A1.
25. C. M. Archer, J. R. Dilworth, P. Jobanputra, R. M. Thompson, M. McPartlin, D. C. Povey, G. W. Smith, and J. D. Kelly, Polyhedron, 1990, 9, 1497.
26. J. R. Dilworth and P. Jobanputra, unpublished work.
27. O. D. Sloan and P. Thornton, Polyhedron, 1988, 7, 329.
28. A. Davison, C. Orvig, H. S. Trop, M. Sohn, B. V. DePamphilis, and A. G. Jones, Inorg. Chem., 1988, 19, 1980.

What is claimed is:

1. A $^{99m}$Tc complex of formula $L_n$Tc=NR, $L_n$Tc—N=NY or $L_n$Tc—(N=NY)$_2$, where:

each L is independently a monodentate or multidentate ligand;

Y is a substituted or unsubstituted aryl group or substituted or unsubstituted alkyl group;

R is Y or the grouping —NR$^1$R$^2$;

n is 1, 2, 3 or 4;

where at least one of R or Y is combined with one or more of the L groups;

R$^1$ and R$^2$ are H, substituted or unsubstituted aryl groups or substituted or unsubstituted aliphatic or cyclic alkyl groups, and is the same or different, provided that both are not hydrogen.

2. A method of preparation of the $^{99m}$Tc complex of claim 1 which comprises the derivatization of a technetium oxo-containing species by condensation with a hydrazine, an amine, an isocyanate, a sulphinylamine or a phosphinimine.

3. A radiopharmaceutical which comprises the $^{99m}$Tc complex of claim 1.

* * * * *